US012143264B2

(12) United States Patent
Adogla et al.

(10) Patent No.: US 12,143,264 B2
(45) Date of Patent: Nov. 12, 2024

(54) MIGRATING EDGE DEVICE RESOURCES TO A CLOUD COMPUTING ENVIRONMENT

(71) Applicant: Oracle International Corporation, Redwood Shores, CA (US)

(72) Inventors: Eden Grail Adogla, Seattle, WA (US); David Dale Becker, Seattle, WA (US); Maxim Baturin, Sammamish, WA (US); Brijesh Singh, Mercer Island, WA (US); Iliya Roitburg, Seattle, WA (US); Abhishek Kar, Chandler, AZ (US)

(73) Assignee: Oracle International Corporation, Redwood Shores, CA (US)

( * ) Notice: Subject to any disclaimer, the term of this patent is extended or adjusted under 35 U.S.C. 154(b) by 476 days.

(21) Appl. No.: 17/581,804

(22) Filed: Jan. 21, 2022

(65) Prior Publication Data

US 2022/0327007 A1 Oct. 13, 2022

Related U.S. Application Data

(60) Provisional application No. 63/173,244, filed on Apr. 9, 2021.

(51) Int. Cl.
*G06F 3/00* (2006.01)
*G06F 3/06* (2006.01)
(Continued)

(52) U.S. Cl.
CPC ........ *H04L 41/0806* (2013.01); *G06F 3/0604* (2013.01); *G06F 3/0622* (2013.01);
(Continued)

(58) Field of Classification Search
CPC ...................................................... G06F 9/50
See application file for complete search history.

(56) References Cited

U.S. PATENT DOCUMENTS 8,613,070 B1 12/2013 Borzycki et al.
10,404,613 B1 9/2019 Brooker et al.
(Continued)

OTHER PUBLICATIONS

Mohamed Azab, MIGRATE: Towards a Lightweight Moving-target Defense against Cloud SideChannels. (Year: 2016).*
(Continued)

*Primary Examiner* — Lechi Truong
(74) *Attorney, Agent, or Firm* — Kilpatrick Townsend & Stockton LLP

(57) ABSTRACT

Techniques are disclosed for migrating one or more services from an edge device to a cloud computing environment. In one example, a migration service receives a request to migrate a first set of services from the edge device to the cloud computing environment. The migration service identifies a hardware profile of a computing device (or devices) of the cloud computing environment that matches the edge device, and then configures the computing device to execute a second set of services that corresponds to the first set of services. The migration service establishes a communication channel between the edge device and the computing device, and then executes a set of migration operations such that the second set of services is configured to execute as the first set of services. The computing device may operate in a virtual bootstrap environment or dedicated region of the cloud computing environment.

17 Claims, 12 Drawing Sheets

(51) Int. Cl.
  *G06F 8/61* (2018.01)
  *G06F 8/658* (2018.01)
  *G06F 9/4401* (2018.01)
  *G06F 9/455* (2018.01)
  *G06F 9/50* (2006.01)
  *G06F 11/14* (2006.01)
  *H04L 9/08* (2006.01)
  *H04L 9/40* (2022.01)
  *H04L 12/46* (2006.01)
  *H04L 41/0806* (2022.01)
  *H04L 67/10* (2022.01)

(52) U.S. Cl.
  CPC .......... *G06F 3/0655* (2013.01); *G06F 3/0659* (2013.01); *G06F 3/067* (2013.01); *G06F 3/0679* (2013.01); *G06F 8/61* (2013.01); *G06F 8/658* (2018.02); *G06F 9/4406* (2013.01); *G06F 9/45558* (2013.01); *G06F 9/505* (2013.01); *G06F 9/5055* (2013.01); *G06F 9/5077* (2013.01); *G06F 9/5088* (2013.01); *G06F 11/1451* (2013.01); *G06F 11/1469* (2013.01); *H04L 9/0897* (2013.01); *H04L 12/4641* (2013.01); *H04L 63/0471* (2013.01); *H04L 63/0478* (2013.01); *H04L 63/0485* (2013.01); *H04L 63/06* (2013.01); *H04L 63/0876* (2013.01); *H04L 63/162* (2013.01); *H04L 63/20* (2013.01); *H04L 67/10* (2013.01); *G06F 2009/45562* (2013.01); *G06F 2009/45587* (2013.01); *G06F 2009/45595* (2013.01); *G06F 2201/84* (2013.01)

(56) References Cited

U.S. PATENT DOCUMENTS

| | | |
|---|---|---|
| 11,683,220 B2 | 6/2023 | Maheshwari et al. |
| 11,777,796 B2 | 10/2023 | Baturin |
| 11,973,643 B2 | 4/2024 | Baturin |
| 2011/0276951 A1* | 11/2011 | Jain ........................ G06F 11/301 718/1 |
| 2013/0332927 A1 | 12/2013 | Tang et al. |
| 2015/0324215 A1* | 11/2015 | Borthakur ........... G06F 9/45558 718/1 |
| 2015/0378753 A1 | 12/2015 | Phillips et al. |
| 2018/0103088 A1 | 4/2018 | Blainey et al. |
| 2019/0007339 A1 | 1/2019 | Bao et al. |
| 2019/0036687 A1 | 1/2019 | Raza et al. |
| 2020/0089515 A1* | 3/2020 | Hari ........................ G06N 3/02 |
| 2021/0132976 A1 | 5/2021 | Chandrappa et al. |
| 2021/0168203 A1 | 6/2021 | Parulkar et al. |
| 2023/0011628 A1 | 1/2023 | Hurley et al. |
| 2023/0049501 A1 | 2/2023 | Xu et al. |

OTHER PUBLICATIONS

U.S. Appl. No. 17/531,566, Notice of Allowance mailed on Mar. 21, 2023, 10 pages.
U.S. Appl. No. 17/569,470, Corrected Notice of Allowability mailed on Jun. 13, 2024, 4 pages.
U.S. Appl. No. 17/569,470, Notice of Allowance mailed on May 17, 2024, 9 pages.
U.S. Appl. No. 17/565,337, Notice of Allowance mailed on May 11, 2023, 11 pages.
U.S. Appl. No. 18/330,227 , Notice of Allowance, Mailed on Mar. 13, 2024, 14 pages.
Li , "Edge Computing, A Compensation Method for Cloud Computing on Smart Grid", The University of New South Wales Sydney, 2020, 95 pages.
U.S. Appl. No. 18/296,348, Non-Final Office Action mailed on Nov. 7, 2023, 10 pages.
U.S. Appl. No. 18/296,348, Notice of Allowance, mailed on Dec. 20, 2023, 5 pages.

* cited by examiner

MIGRATING EDGE DEVICE RESOURCES TO A CLOUD COMPUTING ENVIRONMENT

CROSS-REFERENCE TO RELATED APPLICATIONS

This non-provisional application claims priority to U.S. Patent Application No. 63/173,244, filed on Apr. 9, 2021, entitled "Cloud Computing Edge Computing Device (Rover)," the disclosure of which is herein incorporated by reference in its entirety for all purposes.

BACKGROUND

In cloud computing, processing and storage is generally performed by one or more service providers implemented at a centralized location. Data can be received from customers at the centralized location, processed there, and then the processed (or other) data can be transmitted back to customers. However, having a centralized location for cloud infrastructure components may not be ideal in various scenarios. For example, when there are hundreds or thousands of Internet of Things (IoT) devices transmitting data to the central servers, and especially when those IoT devices are not geographically close to the cloud infrastructure computing devices, conventional centralized systems are not ideal. These IoT devices may be considered on the "edge," as in they are not close to the central servers.

Additionally, there may be other instances when the centralized location for cloud components is less than ideal. For example, if the data is collected (e.g., by IoT devices) in a disconnected region or a location with no Internet connectivity (e.g., remote locations). Current centralized cloud computing environments may not meet time sensitivity requirements when streaming data due to the inherent latency of their wide-area network connections. Remotely generated data may need to be processed more quickly (e.g., to detect anomalies) than conventional centralized cloud computing systems allow. Thus, there are challenges with managing a traditional cloud computing environment that relies on centralized components.

In some cases, when some computing operations are offloaded from a centralized location to a disconnected region, it may be challenging to coordinate subsequent computing operations with respect to the centralized location and the disconnected region. For example, if a customer later wants to migrate one or more of the previously offloaded computing operations back to the centralized location, it may be challenging to perform the migration so as to ensure reliable continuity of those computing operations.

BRIEF SUMMARY

Techniques are provided (e.g., a method, a system, non-transitory computer-readable medium storing code or instructions executable by one or more processors) for resource migration (e.g., including migrating one or more services and/or associated instances, workloads, state, metadata, etc.) from an edge device to a cloud computing environment (e.g., a customer data center and/or a centralized cloud computing environment). The edge device may execute a first set of one or more services in an isolated computing environment that may be separate from the cloud computing environment that provides a plurality of services for executing customer workloads. In some embodiments, upon receiving a request, a migration service may facilitate (e.g., orchestrate) a migration process to migrate resources (e.g., one or more services and/or associated instances, workloads, state data, metadata, etc.) from the edge device to the cloud computing environment, such that, upon completion of the migration process, a dedicated region of the cloud computing environment is configured to execute a second one or more services as the first one or more services (e.g., using the resources migrated from the edge device).

In one example, a system of one or more computers can be configured to perform particular operations or actions by virtue of having software, firmware, hardware, or a combination of them installed on the system that in operation causes or cause the system to perform the actions. One or more computer programs can be configured to perform particular operations or actions by virtue of including instructions that, when executed by data processing apparatus, cause the apparatus to perform the actions. One general aspect includes a computer-implemented method. The computer—implemented method may include receiving, by a migration service of a cloud computing environment, a request to migrate one or more services (and/or resources associated with one or more services) from an edge device to the cloud computing environment, the edge device being associated with a first hardware profile and configured to selectively execute within an isolated computing environment separate from the cloud computing environment. The method also may include identifying, by the migration service, that a second hardware profile of the cloud computing environment (e.g., a hardware profile of a computing device implementing a virtual bootstrap environment, a hardware profile of a computing device implementing a dedicated region, etc.) matches the first hardware profile associated with the edge device. The method also may include identifying a first set of services (and/or resources) associated with the edge device. The method also may include configuring, at a computing device of the cloud computing environment (e.g., a computing device implementing a virtual bootstrap environment, a computing device implementing a dedicated region, etc.), a second set of services corresponding to the first set of services associated with the edge device. The method also may include establishing a communication channel between the edge device and the computing device. The method also may include executing, by the migration service, a set of migration operations associated with migrating resources of the first set of services from the edge device to the cloud computing environment, where migrating the resources configures the second set of services to execute as the first set of services from the cloud computing environment. Other embodiments of this aspect include corresponding computer systems, apparatus, and computer programs recorded on one or more computer storage devices, each configured to perform the actions of the methods.

Implementations may include one or more of the following features. For example, one feature may correspond to the computer-implemented method where executing the set of migration operations further may include: instructing the edge device to disable resource mutations associated with the first set of services executing at the edge device, where disabling resource mutations may include transitioning each of the first set of services to execute in a read-only mode; adjusting, by the migration service, at least a portion of default configuration data of the cloud computing environment to match the service metadata migrated from the edge device; and configuring the second set of services of the cloud computing environment to accept traffic previously intended for the first set of services of the edge device. In some embodiments, executing the set of migration operations further may include: obtaining, by the migration service, first state data that corresponds to a current state of the first set of services associated with the edge device; obtaining, by the migration service, second state data that corresponds to a current state of the second set of services associated with the cloud computing environment; comparing, by the migration service, the first state data with the second state data to validate that the current state of the second set of services matches the current state of the first set of services; and in accordance with determination of a successful validation, configuring the second set of services of the cloud computing environment to accept traffic previously intended for the first set of services of the edge device.

In some embodiments, the edge device may be a first edge device of a plurality of edge devices collectively configured to operate as a distributed computing cluster, the distributed computing cluster associated with a particular namespace, and where the method further may include: configuring the cloud computing environment with a third set of services corresponding to a second edge device of the plurality of edge devices of the distributed computing cluster; establishing a second communication channel between the second edge device of the distributed computing cluster and a second cloud computing environment (e.g., another virtual bootstrap environment, another dedicated region, etc.) associated with the dedicated region; and executing, by the migration service, a second set of migration operations associated with migrating corresponding resources (e.g., metadata) of a fourth set of services from the second edge device to the second cloud computing environment, where migrating the corresponding resources (e.g., metadata) of the fourth set of services to the second cloud computing environment configures the third set of services of the cloud computing environment to execute as the fourth set of services from within the cloud computing environment. In some embodiments, the computer-implemented method may include: initializing, based at least in part on predefined protocol, an additional service within the cloud computing environment; determining that the additional service has no corresponding service executing on the edge device; and configuring the additional service with data that is different from the service metadata migrated from the edge device. In some embodiments, the computer-implemented method may include: accessing a manifest file associated with the edge device, the manifest file identifying the first hardware profile of the edge device and the first set of services executing at the edge device. In some embodiments, executing the set of migration operations further may include: executing, by the migration service, one or more service-specific migration protocols, a particular migration protocol being associated with migrating resource data of a particular service of the first set of services from the edge device to the cloud computing environment. Implementations of the described techniques may include hardware, a method or process, or computer software on a computer-accessible medium.

Some embodiments disclose a computing system of a cloud service provider comprising a memory comprising computer-executable instructions that, when executed with one or more processors of the computing system, cause the computing system to perform the method disclosed above.

Some embodiments disclose a non-transitory computer-readable storage medium comprising computer-executable instructions that, when executed with one or more processors of a computing system (e.g., a computing system of a cloud service provider), cause the computing system to perform the method disclosed above.

DETAILED DESCRIPTION

Figure 1:
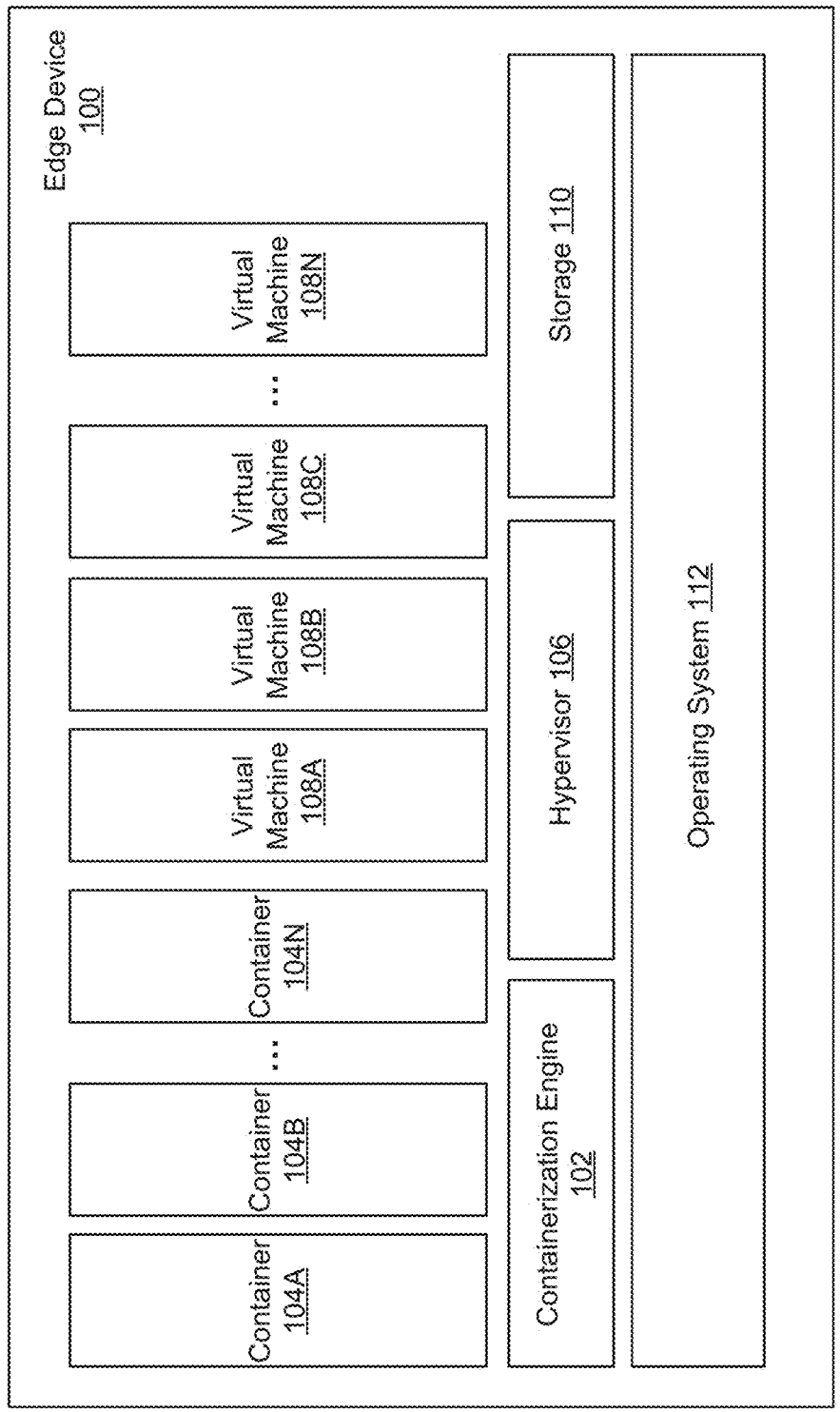
FIG. 1 is a block diagram of an example high-level architecture for a cloud infrastructure edge computing device, according to at least one embodiment.

In the following description, various embodiments will be described. For purposes of explanation, specific configurations and details are set forth in order to provide a thorough understanding of the embodiments. However, it will also be apparent to one skilled in the art that the embodiments may be practiced without the specific details. Furthermore, well-known features may be omitted or simplified in order not to obscure the embodiment being described.

Introduction

In some examples, a cloud-integrated edge service (e.g., implemented in an edge computing device) may be integral in addressing the desire to run time-sensitive cloud infrastructure application outside of a centralized data center (e.g., a datacenter of a cloud infrastructure service provider).

Such an edge computing device may deliver computing and storage at the edge and/or in disconnected locations (e.g., remote locations separate from the centralized data center and lacking a public/private network connection (e.g., an Internet connection, a VPN connection, a dedicated connection, etc.) to enable low-latency processing at or near the point of data generation and ingestion. In some instances, a fleet of portable (which may be ruggedized for protection) server nodes (e.g., a fleet of edge devices) may be configured to physically bring the cloud infrastructure service to remote locations where cloud technology has been considered technologically infeasible or too cost prohibitive to implement.

To a customer (e.g., a user), the edge computing device can act as an extension of their cloud infrastructure: including virtual machines (VMs), containers, functions and data files, block volumes or object store services can also be delivered from the cloud infrastructure tenancy (e.g., a tenancy of the centralized cloud computing environment) with little to no modifications, and the customer experience may remain unchanged from that of the centralized cloud computing experience. Additionally, the edge computing device may be configured to implement both a control plane and a data plane that are part of a cloud infrastructure service provider. The data plane can be configured to manage data storage, migration, processing, etc., while the control plan can be configured for controlling the various services and architecture components of the computing device. Once the edge computing device is properly connected to a customer computing device (e.g., via a local area network (LAN)), the customer may be able to utilize the IaaS service (or at least a subset of it) using the same SDK and API used with the centralized cloud service.

The edge computing device can be delivered to a customer in a pre-configured form, such that the only action that might be required of the customer is to connect the nodes to a network (e.g., a local/on premise network that is accessible by a user computing device), power them up, and/or log in. The device can be pre-configured in various ways based on customer preference/request, or it can be in one of various configurations (e.g., storage-centric, compute-centric, etc.). The node or cluster of nodes can be portable and is intended to be mobile—when moved and set up again (or used while in motion), the deployment continues to run from where it turned off (or continuously). The edge computing device can also monitor for wide area network (WAN) connection availability (e.g., the Internet or the like), and can synchronize customer and management data with the cloud once connected to a WAN.

Some potential use cases for the edge computing device include: storage and processing, compute and input/output (I/O) intensive applications, machine learning, remote computing, low latency database and analytics, and data collection and migration. More specifically, the edge device can be used for storage and processing of large volumes of images, video, audio, and IoT sensor data generated in environments where WAN connection is latent or unavailable (e.g., in remote areas, an oil off-shore platform, or the like). Once this data is pre-processed, filtered, compressed, and/or secured it may be transported or transferred to the cloud service provider, where it can be further processed by the centralized server (e.g., traditional cloud service provider). The device can also be used for compute and I/O intensive applications, where low latency is paramount, such as tactical reconnaissance or 5G communications. The device can also be used for machine learning, with models trained in the cloud and running in disconnected locations to improve efficiency, intelligence, and/or productivity in manufacturing, document management, transportation, oil and gas mining, and/or telecommunications. It can also be used for remote computing requiring elevated security and airtight containment of data. Additionally, the device can be used for low latency database and analytics workloads, with more applications optimized over time. Further, the device can also be used for data collection and migration of large sets of object and database management system (DBMS) data into a cloud service provider, e.g., at faster speeds and lower cost than a WAN transfer.

The edge device can natively support distributed cloud paradigms, where complex, multi-stage compute workflows can be separated into individual components, which in turn can be deployed to the infrastructure of the edge device, on premise, and/or in the cloud. An example of such distributed workflow is represented in the following scenario. Massive amounts of data can be collected by an edge computing node deployed on an airplane (e.g., a military jet) in a reconnaissance operation with no Internet access (e.g., a disconnected edge computing device), where this data is be pre-processed in near real time by a machine learning model previously trained by the cloud service provider that provided the edge device. Even the first pass of processing the data with the models can detect significant anomalies and can alert personnel immediately—for example, a bridge may be destroyed and therefore the troops should be rerouted. When the airplane lands, the edge computing device can be physically connected to a network (e.g., an edge station potentially deployed at the airstrip). The pre-processed, filtered, smaller dataset can be loaded for final processing to a cluster of edge computing device nodes at the edge station. The original edge computing device can be released and can be loaded on another (or the same) airplane, for example to support the next mission. When processing at the edge station is complete, a 3D map update can be issued for immediate use. Change sets can then be uploaded by the edge station cluster to a datacenter and can be used to build future models providing intelligent tactical forecasts to the reconnaissance operation, or the like.

It should be appreciated that the following techniques may be employed in a variety of contexts such as telecommunications, oil and gas, healthcare, hospitality, agriculture, transportation, and logistics, and the like.

Embodiments described herein address these and other problems, individually and collectively. Specifically, embodiments of the present disclosure provide for a cloud infrastructure edge computing device.

Edge Device Architecture

An edge computing device (sometimes referred to as "a cloud edge device" or an "edge device," for brevity), extends a user's centralized cloud computing tenancy by physically putting customer infrastructure and platform services where data is generated—on the edge, on premise, or completely disconnected. Each deployment is created to address specific customer needs by provisioning VM instance images and data from the customer's centralized cloud tenancy. These workloads remain fully functional offline as the edge device adapts to the connection state, operates in harsh environmental conditions, and is ready to sync with the cloud whenever the connection is re-established.

FIG. 1 is a block diagram of an example high-level architecture for a cloud infrastructure edge computing device (e.g., edge device 100), according to at least one embodiment. An overview of the software and hardware component of the edge device 100 is provided below.

In some examples, the edge device 100 may include containerization engine 102 (e.g., Docker, Kubernetes, etc.) configured to implement one or more containers (e.g., corresponding to service(s) 104A, 104B, 104C, to 104N, collectively referred to as "service(s) 104"). A containerization engine (e.g., the containerization engine 102) may be container-orchestration system for automating computer application deployment, scaling, and management. In some embodiments, the containerization engine may be configured to provide OS-level virtualization to deliver software in packages called containers. These containers can be isolated from one another and utilize respective software, libraries, and configuration files, and can communicate with each other through well-defined channels. In some embodiments, service(s) 104 may include any suitable number of services (e.g., one or more). These services may implement at least some portion of centralized cloud capabilities. Each service may be stand-alone or operate as a distributed cluster. The edge device 100 may further include a hypervisor 106 configured to implement one or more virtual machines (e.g., virtual machines 108A, 108B, 108C, to 108N, collectively referred to as "virtual machine(s) 108" or "VMs 108").

In some examples, the edge device 100 includes storage 110 (e.g., object and/or block storage for storing local data). The edge device 100 includes operating system (OS) 112. In some embodiments, the OS 112 may be optimized for executing on an edge device and/or specific to execution on an edge device. OS 112 may be configured to manage the hardware of edge device 100 and supports a data plane of the services running on the edge device 100. The OS 112 may be configured to support a specific deployment type (e.g., a single edge device deployment, or a specific edge device cluster configuration). The OS 112 may be configured to secure the edge device by disallowing direct access by customers.

In some embodiments, the edge device 100 may include hardware such as any suitable number of central processing units (CPUs) and/or storage drives. For example, the edge device 100 depicted in FIG. 1 may have one, two, or more CPUs, with various numbers of cores per processing unit, and it may include any number of storage drives (e.g., 6.4 terabyte (TB) drives, or the like). As a non-limiting example, the edge device 100 may include block and/or object storage of any suitable size. The edge device 100 may include any suitable number of central processing units (CPUs), graphics processing units (GPUs), random access memory (RAM) of any suitable size, one or more ports (e.g., QSFP28, RJ45, dual ports, etc.), tamper-evident seals, or any suitable combination of the above components.

In some examples, the basic system functionality/services can be accessed via RESTful APIs have a custom load of software based on Linux. The virtual machine(s) 108 may individually be a Kernel-based Virtual Machines (KVM) (e.g., a virtual machine managed by a virtualization module in the Linux kernel that allows the kernel to function as a hypervisor) and/or a hardware-based Virtual Machine (e.g., a virtual machine managed by a virtualizer, such as Quick EMUlator (QEMU), that can perform hardware virtualization to enable virtual machines to emulate of number of hardware architectures). Although storage 110 is represented as a separate component from the container(s) 104 and VM(s) 108, it can run as a container (e.g., container 104A) or in a VM (e.g., VM 108A). In some examples, it may be favorable to implement the storage 110 (e.g., object storage, block storage, etc.) as a container.

Figure 2:
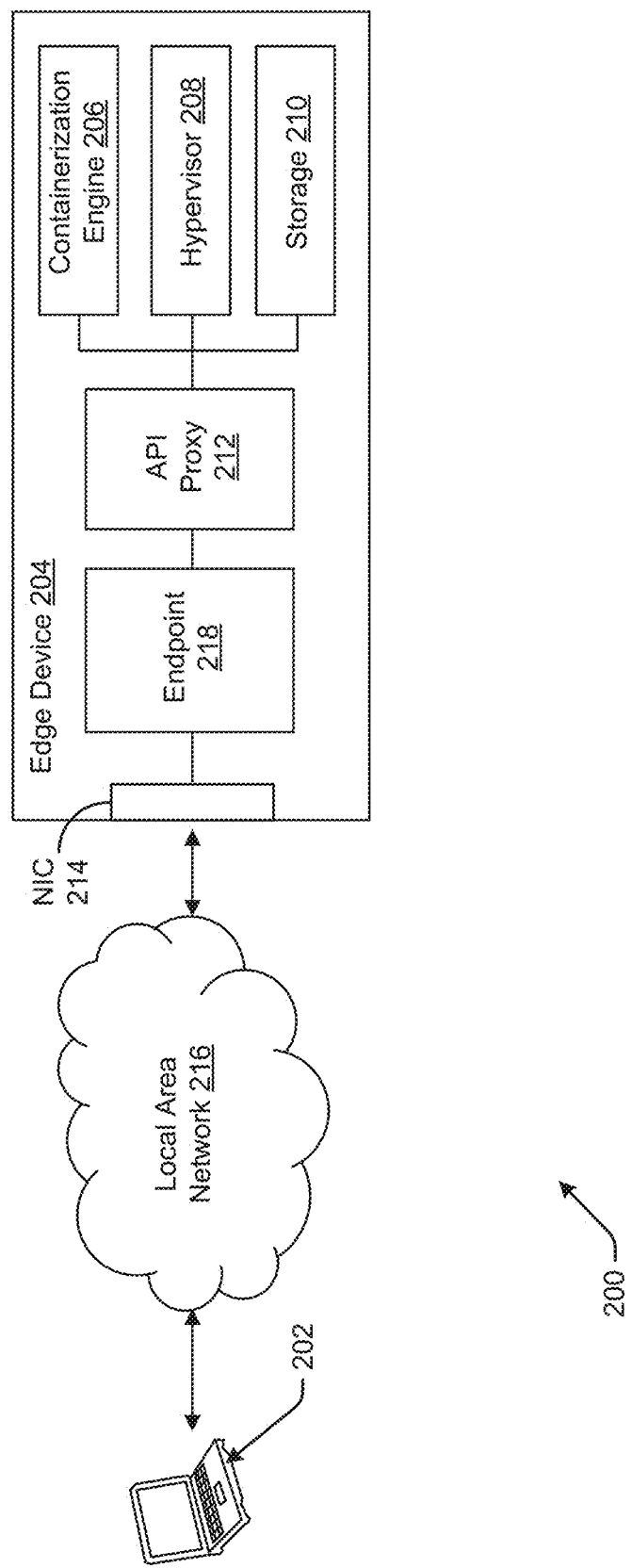
FIG. 2 is a block diagram of an example architecture for connecting a user computing device to a cloud infrastructure edge computing device, according to at least one embodiment.

FIG. 2 depicts an example architecture 200 for connecting the edge device described herein (e.g., edge device 100 from FIG. 1) to a computing device 202 (e.g., a user computing device). The computing device 202 can be any type of computing device including, but not limited to, a laptop computer, a desktop computer, or the like. The edge device 204 (an example of the edge device 100 of FIG. 1) may include containerization engine 206 (an example of the containerization engine 102 of FIG. 1), hypervisor 208 (an example of the hypervisor 106 of 1), and storage 210 (an example of the storage 110 of 1).

Additionally, as mentioned briefly above, the edge device 100 may include an API proxy 212 for managing the RESTful API calls received from the computing device 202. The API calls may enter the edge device 204 via network interface card (NIC) 214 that is internal to the edge device 204. The network interface card 214 may be used to connect the edge device 204 to the computing device 202 via a local area network (e.g., the LAN 216). The API calls received by the NIC 214 may be transmitted to an exposed endpoint that may implement a Web server (e.g., endpoint 218). The web server can transmit the requests to the API Proxy 212, which can route the requests to the appropriate service (e.g., containerization engine 206, hypervisor 208, and/or storage 210). The exposed endpoint/web server may also be configured to implement the lightweight console that is for use by the customer (e.g., the user interface displayed on the computing device 202).

The lightweight console can run within a web browser (e.g., Mozilla Firefox, or the like) on a laptop computer, desktop computer, or other network-accessible device (e.g., connected to the local area network (LAN 216)) that is network-connected to the edge device 204 (e.g., via a router, cable, etc.). The edge device 204 can expose the endpoint 218 for the console connection, and the web server can transmit data to the web browser of the computing device 202 over the LAN 216.

Figure 3:
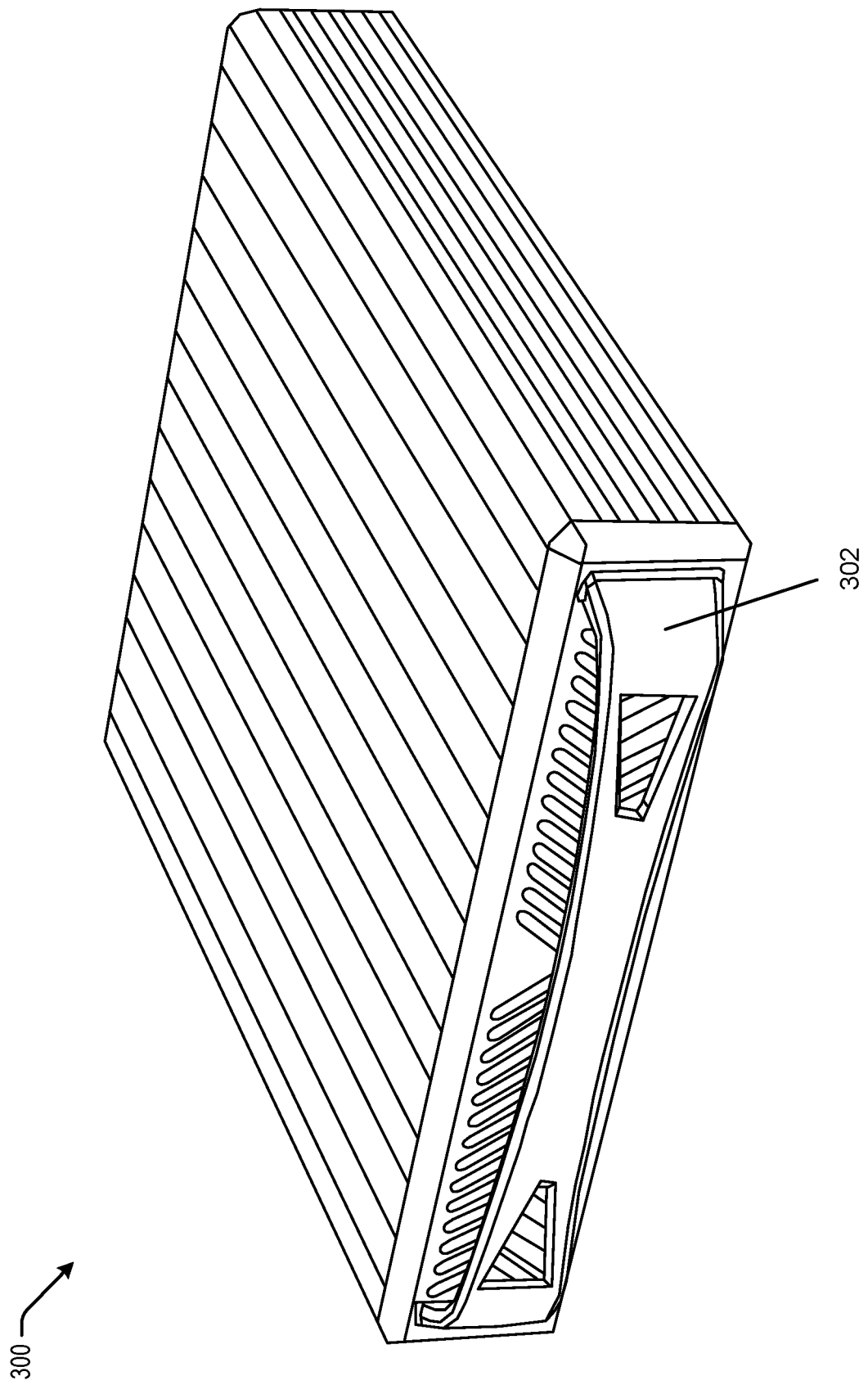
FIG. 3 is a block diagram of an example enclosure for a cloud infrastructure edge computing device, according to at least one embodiment.

FIG. 3 illustrates an example physical enclosure 300 of the edge device described herein (e.g., edge device 100 from FIG. 1). Various different form factors, shapes, colors, etc., can be employed to build a box (e.g., ruggedized) that can house the edge computing device. The physical enclosure can include handle 302, as shown, and may include tamper evident elements, so that if anyone breaks the enclosure open, it will be evident. In this way, the service provider that provides the edge computing device can ensure that the device is not modified. In some examples, the physical enclosure 300 may not be possible to open. However, in some cases, it might be possible, but it would require extreme measures.

Figure 4:
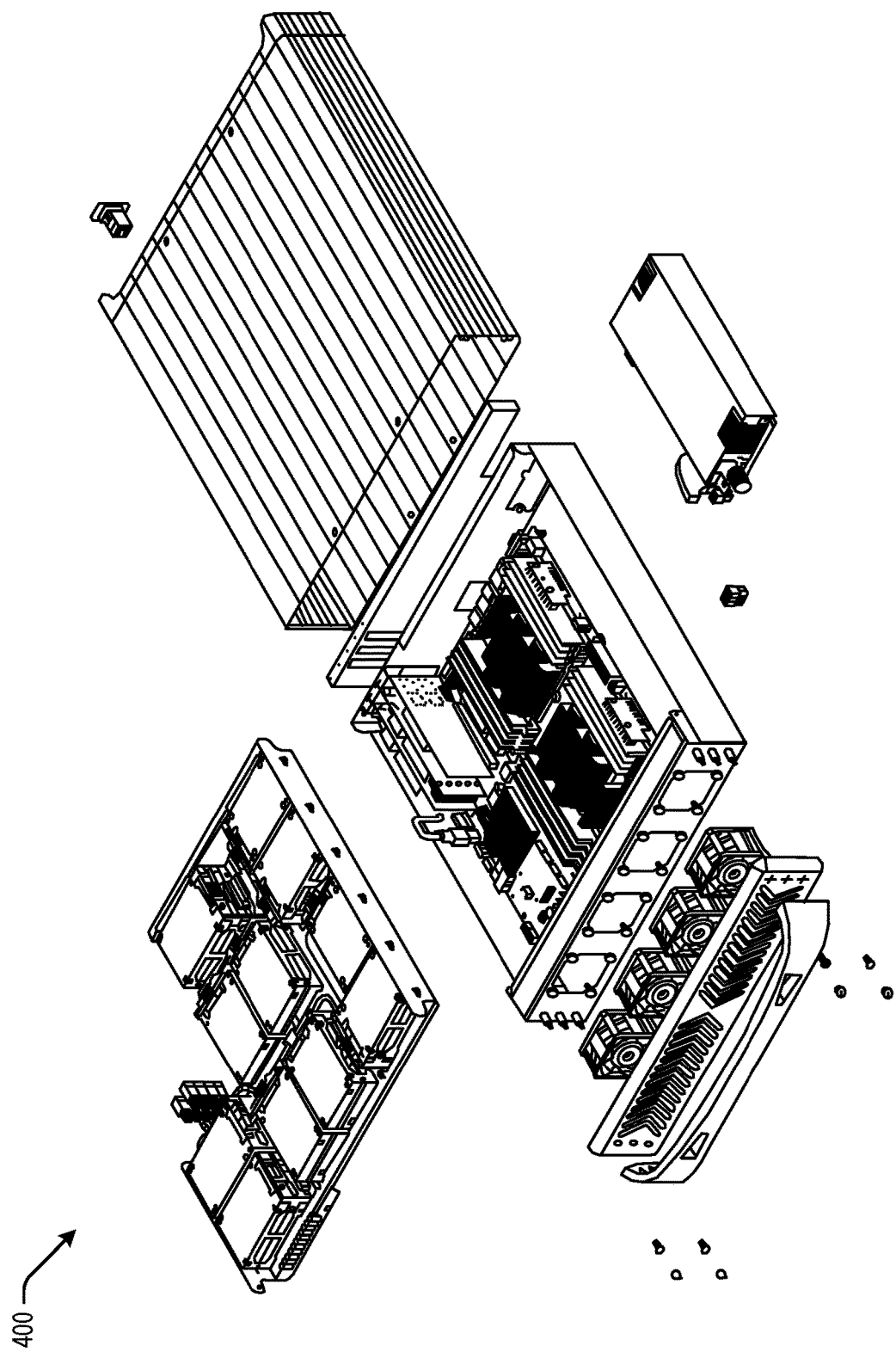
FIG. 4 illustrates an exploded view of the cloud infrastructure edge computing device described herein, in accordance with at least one embodiment.

FIG. 4 illustrates an exploded view of the cloud infrastructure edge computing device described herein (e.g., edge device 400, an example of the edge device 100 of FIG. 1), in accordance with at least one embodiment. The various components described with respect to FIGS. 1 and 2 can be communicatively attached to one or more motherboards and/or interface cards within the edge computing device 400. The illustrated configuration of components is but just one implementation. The specific locations of components shown is not intended to be limiting, and as noted, any configuration that is capable of implementing the functionality described herein is acceptable. Once the components are installed, the entire box can be closed, sealed, and locked with tamper-evident components.

The edge device 400 is a single enclosure. The enclosure may be designed to house any suitable number of serially attached SCSI (SAS) solid-state drives (SSDs) and all other components (e.g., CPU, memory, GPU, etc.) within the enclosure. The system may include one or more (e.g., 12 Gb) SAS connections to each drive in a fully contained sheet metal enclosure designed to fit within a standard 19" rack resting on an L bracket/shelf, on a table top or upright next to a desk with the use of a floor stand.

The system may include a tamper evident enclosure, front security plugs covering screws holding a front bezel in place with rear security interlock features. In some embodiments, the system may include a dual socket motherboard and any suitable amount of DRAM. In some embodiments, the system may include any suitable number (e.g., 2, 3, etc.) SATA SSDs, storage controllers, embedded network connections, one or more ports (e.g., dual ports, serial ports, etc.), one or more fans as part of a cooling system, or any suitable combination of the above.

As a non-limiting example, the edge device 400 may be made up of an external extruded aluminum case secured in the front with a vented bezel and rear panel only exposing I/O connections required for data transfer and management. Mounting can be designed to mount the any suitable motherboard, fans, and power supply.

Figure 5:
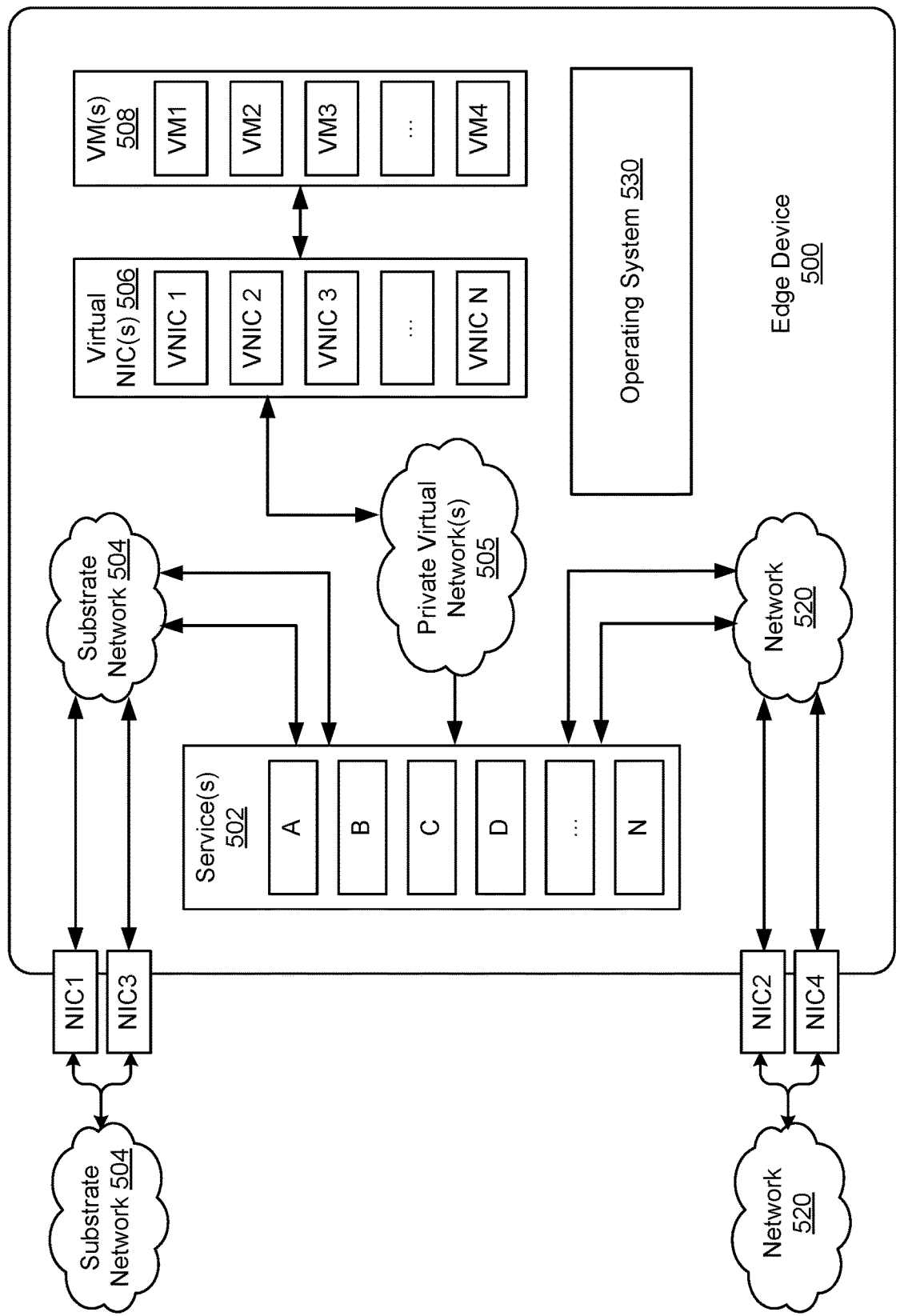
FIG. 5 is a block diagram of an example computer architecture of a cloud infrastructure edge computing device, according to at least one embodiment.

FIG. 5 is a block diagram of an example computer architecture 500 of a cloud infrastructure edge computing device (e.g., edge device 500, an example of the edge devices 100 and 204, of FIGS. 1 and 2, respectively), according to at least one embodiment. The edge device 500 can be thought of as a cloud-integrated service that extends some or all of conventional cloud capabilities to locations outside of cloud data centers. This can be achieved via portable ruggedized server nodes that provide cloud-like functionality in locations with no WAN connectivity. This allows customers to shift select cloud workloads to remote locations and enable intensive data processing operations close to the data ingestion points at the edge of their cloud infrastructure.

The edge device 500 may include any suitable number of services (e.g., service(s) 502). Each service may run as a container (e.g., a Docker container) locally on the edge device 500. The service(s) 502 may be communicatively connected via a substrate network 504 such that the communications between services are encrypted (e.g., in accordance with a security protocol such as MACsec). Each container may be assigned a substrate IP address (e.g., a static address) with which traffic can be addressed. In some embodiments, a security protocol (e.g., MACsec) is configured at provisioning time (e.g., before the edge device 500 is shipped to the user). The edge device's system software (including service(s) 502) may execute in the secure environments protected by boot security software (e.g., Trenchboot Secure Launch). Users may be restricted from accessing the secure environment and/or the substrate network 504. To minimize the amount of resources used by these services the service code may be compiled and saved to disk to decrease RAM space as well as decrease the CPU load on the edge device 500.

Some example services included in service(s) 502 may include a UI console service, an identity control plane (CP) service, an identity data plane (DP) service, a compute application programming interface (API) service, a compute worker thread service, a virtual network (VN) API service, a block storage API service, a function-as-a-service service, an events service, an object storage management service (e.g., implementing a storage platform such as Ceph Storage), a compute DP service (e.g., an example of hypervisor 208 of FIG. 2), a VN DP service, a block storage management service, a function-as-a-service API service, a function-as-a-service load balancing (LB) service, a function-as-a-service process thread service, a distributed data store management service (e.g., etcd3), a dynamic host configuration protocol service, a domain name system service, a network time protocol (NTP) service, to name a few. Some example functionality provided by these services is discussed below.

By way of example, compute DP service may be configured (e.g., preconfigured and provisioned onto the edge device 500) to isolate the VM(s) 508 on the same hypervisor host. The compute DP service can utilize any suitable container engine (e.g., Docker container, MicroContainer, or the like) to isolate the VM(s) 508 on the same hypervisor host from each other. The compute DP service may utilize any suitable hypervisor (e.g., Quick EMUlator (QEMU), Kernel-based Virtual Machine (KVM), etc.) to provide virtual hardware emulation for VM(s) 508. In some embodiments, VNIC(s) 506 are attached to subnets of any suitable number of virtual networks (e.g., private virtual network(s) (PVN(s))) 505 and are assigned private Internet Protocol (IP) addresses. One VM may have multiple VNICs from different VCNs and different subnets. The maximum number of VNICs can be limited by predefined thresholds (e.g., configuration data referred to as "VM shape" that defines VNICs per VM count, VNIC shape, etc.). In some embodiments, the predefined thresholds are applied to each of the VM(s) 508. The subnets utilized by the VNIC(s) 506 may be isolated by VLANs. In some embodiments, some or all of the VNIC(s) 506 may be assigned public and/or private IP addresses. A public IP address is an address in the network(s) 520, while a private IP address refers to an IP address of the PVN(s) 505.

In some embodiments, the edge device 500 implements various networking functionality via a number of services such as a network address translation (NAT) service, a dynamic host configuration protocol (DHCP) service, a domain name system (DNS) service, a network time protocol (NTP) service, a metadata service, and a public API service). The metadata service may provide initialization data and other metadata to all VM(s) 508. In some embodiments, DHCP service assigns private IP addresses to each of the VNIC(s) 506, each of the VM(s) 508 having one or more VNICS. DNS service may provide domain name resolution to VM(s) 508 on the edge device 500. NTP may provide time synchronization to VM(s) 508. In some embodiments, a public IP service executing as part of service(s) 502 may enable a VM to access a public API without assigning the VM a public IP and without configuring a service gateway.

In some embodiments, at least one of the VM(s) 508 may implement block (or object) storage. In some embodiments, the hypervisor associated with a virtual machine may include a library that enables the hypervisor to use a distributed data storage platform (e.g., Ceph). The library may utilize a protocol associated with that storage platform (e.g., RADOS Block Device (RBD) to facilitate storage of block-based data. The distributed data storage platform may be implemented over multiple virtual machines. In some embodiments, the distributed data storage platform supports making snapshots and copying block volumes. VM images and VM block volumes can be Ceph block devices. In some embodiments, the VM(s) implementing the distributed data storage platform will use system reserved resources (e.g., 8 CPU cores, some of the total number of CPUs available on the edge device 500). For example in order to provision a boot volume, a block device image may be copied to a boot volume of the block device. The distributed data storage platform may use block devices include multiple nodes for redundancy. If some node fails then the block device can continue to operate. In some embodiments, the distributed data storage platform (e.g., Ceph), automatically recovers the block device data in case of a few node failures. Block storage may be utilized to store images for any suitable deployable resource. By way of example, an image may be utilized for launching VMs. In some embodiments, the image may correspond to a particular VM shape (e.g., a compute heavy VM, a GPU optimized VM, a storage VM, and the like).

Compute API service may support the following operations: 1) VM launch and terminate, 2) VM stop, start, reboot, 3) List VMs and/or get information on a specific VM, 4) obtain VM console history API, 5) obtain a VM snapshot, 6) attach/detach block volumes, and the like. In some embodiments, Compute API service can be used to call other services (e.g., compute DP service, identity DP service for authentication and authorization, etc.).

Some of the functionality of other services will be discussed in connection with FIG. 7. In general, although each service may not be discussed in detail herein, the general functionality provided by the service(s) 502 may include the functionality of cloud services provided by a remote cloud service provider. In some embodiments, the edge device 500 may be associated with a predefined region and/or realm such that some of the service(s) 502 may operate as if they were operating in a cloud computing environment, despite the fact they are operating on one or more local device(s) (one or more edge devices) as a single instance or as part of a distributed service that may have no or intermittent public network access to a cloud computing environment associated with the customer.

In some embodiments, the edge device 300 may provide any suitable number of virtual networks (e.g., private virtual network(s) 505) using compute, memory, and networking resources (e.g., virtual network interface card(s) (VNIC(s) 506)). A virtual network is a logical network that runs on top of a physical substrate network. Using the service(s) 502, one or more customer resources or workloads, such as virtual machines (e.g., virtual machine(s) (VM(s)) 508, executing a compute instance) can be deployed on these private virtual networks. Any suitable combination of VM(s) 508 can execute functionality (e.g., a compute instance, storage, etc.) which is individually accessible through a virtual NIC (e.g., one of the virtual NIC(s) 506). Each VM that is part of a PVN is associated with a VNIC that enables the VM (e.g., a compute instance) to become a member of a subnet of the PVN. The VNIC associated with a VM facilitates the communication of packets or frames to and from the VM. A VNIC can be associated with a VM when the VM is created. PVN(s) 505 can take on many forms, including peer-to-peer networks, IP networks, and others. In some embodiments, substrate network traffic of the service(s) 502 may be encrypted and/or isolated (e.g., by virtue of different PVNs or subnets) from network traffic of one or more the VM(s) 508 executing on the edge device 500.

The edge device 500 thus provides infrastructure and a set of complementary services that enable customers to build and run a wide range of applications (e.g., compute instances), services, and/or storage in a highly available, physically local, and virtual hosted environment. The customer does not manage or control the underlying physical resources provided by the edge device 500 but has control over expanding or reducing virtual machines (e.g., compute instances, virtual NICs, block or object storage, etc.), deploying applications to those virtual machines, and the like. All workloads on the edge device 500 may be split into different CPU sets (e.g., VM and non-VM). One set (e.g., non-VM such as workloads performed by the service(s) 502) may utilize a subset of CPU cores (e.g., 8) of the edge device 504, while the other set (e.g., VM workloads performed by the VM(s) 508) may utilize a different subset of CPU cores.

The edge device 500 may be communicatively connected to a user device (e.g., the computing device 202 of FIG. 2) via one or more network interfaces (e.g., NIC2 and/or NIC 4) and network 520 to interact and/or manage the VM(s) 508. In certain embodiments, a lightweight console can be provided at the user device via a web-based user interface that can be used to access and manage the edge device 500. In some implementations, the console is a web-based application (e.g., one of the service(s) 502) provided by the edge device 500.

FIG. 5 depicts a single edge device. However, it should be appreciated that more than one edge device may be utilized as a distributed computing cluster.

Figure 6:
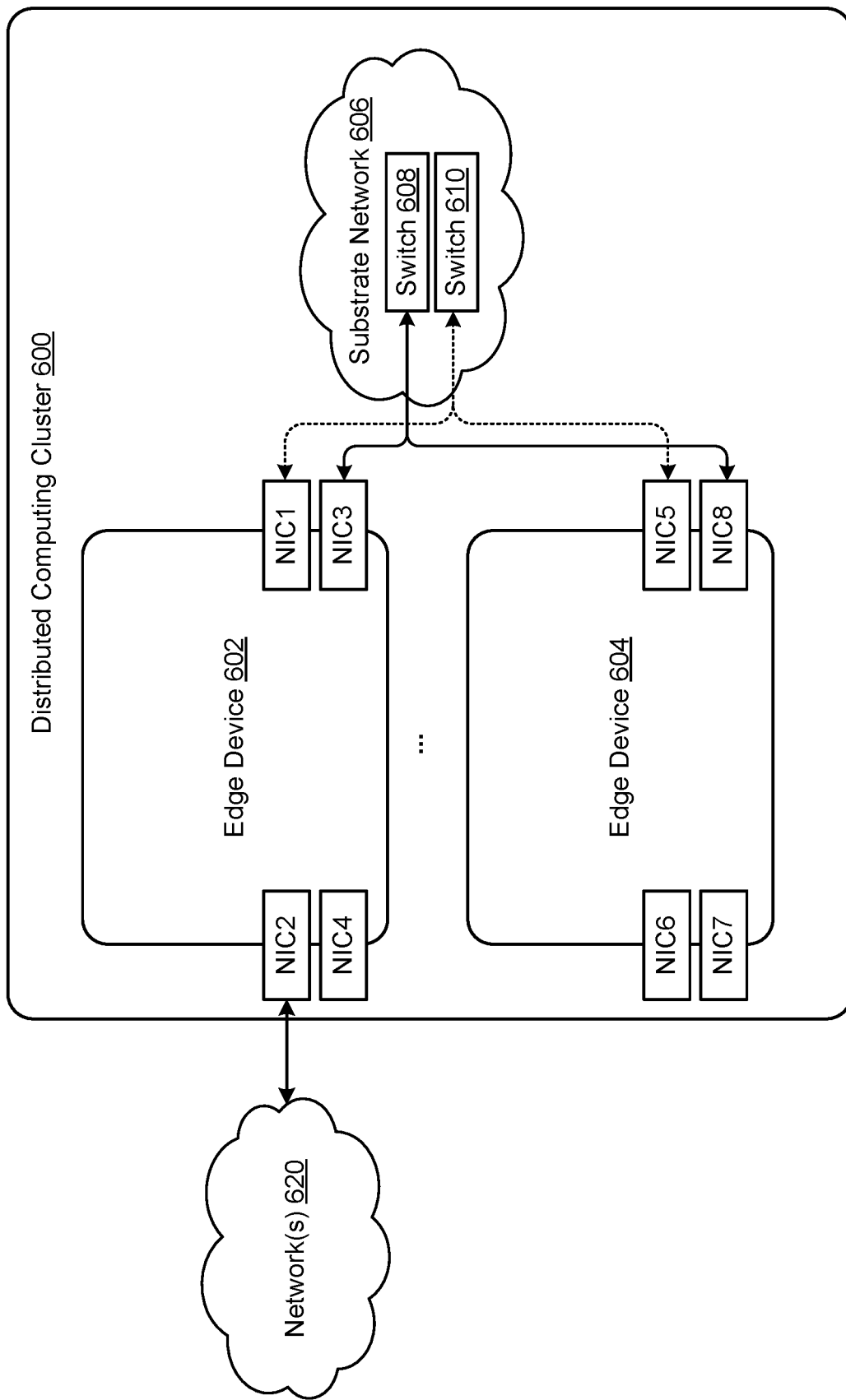
FIG. 6 is a block diagram depicting a distributed computing cluster that includes one or more edge computing devices, according to at least one embodiment.

FIG. 6 is a block diagram depicting a distributed computing cluster 400 that includes one or more edge computing devices (e.g., edge device 602 and 604, each an example of the edge device 500 of FIG. 5), according to at least one embodiment.

Each edge device of the distributed computing cluster 600 may be connected via substrate network 606 (an example of the substrate network 504 of FIG. 5. In some embodiments, the edge devices of the distributed computing cluster 600 (sometimes referred to as "edge computing nodes" or "edge nodes") may be connected by the substrate network 606 using one or more switches (e.g., switch 608 and/or 610). In some embodiments, NIC1 and NIC5 may include a particular connector (e.g., RJ45 connector) while NIC3 and NIC8 may include the same or a different connector (e.g., a QSFP28 100 GbE connector). In some embodiments, only one edge device of the distributed computing cluster 600 is connected to a customer network such as network(s) 620 (an example of the network(s) 520 of FIG. 5). Thus, not only may traffic between services of an edge device be encrypted and isolated from other traffic of a given edge device, but traffic between distributed services operating across multiple edge devices may also be encrypted and isolated from other traffic of the computing cluster. In some embodiments, each edge device is preconfigured as a particular node in the distributed computing cluster 400. In other embodiments, the user can configured the number and topology of the edge devices of the distributed computing cluster 600.

Figure 7:
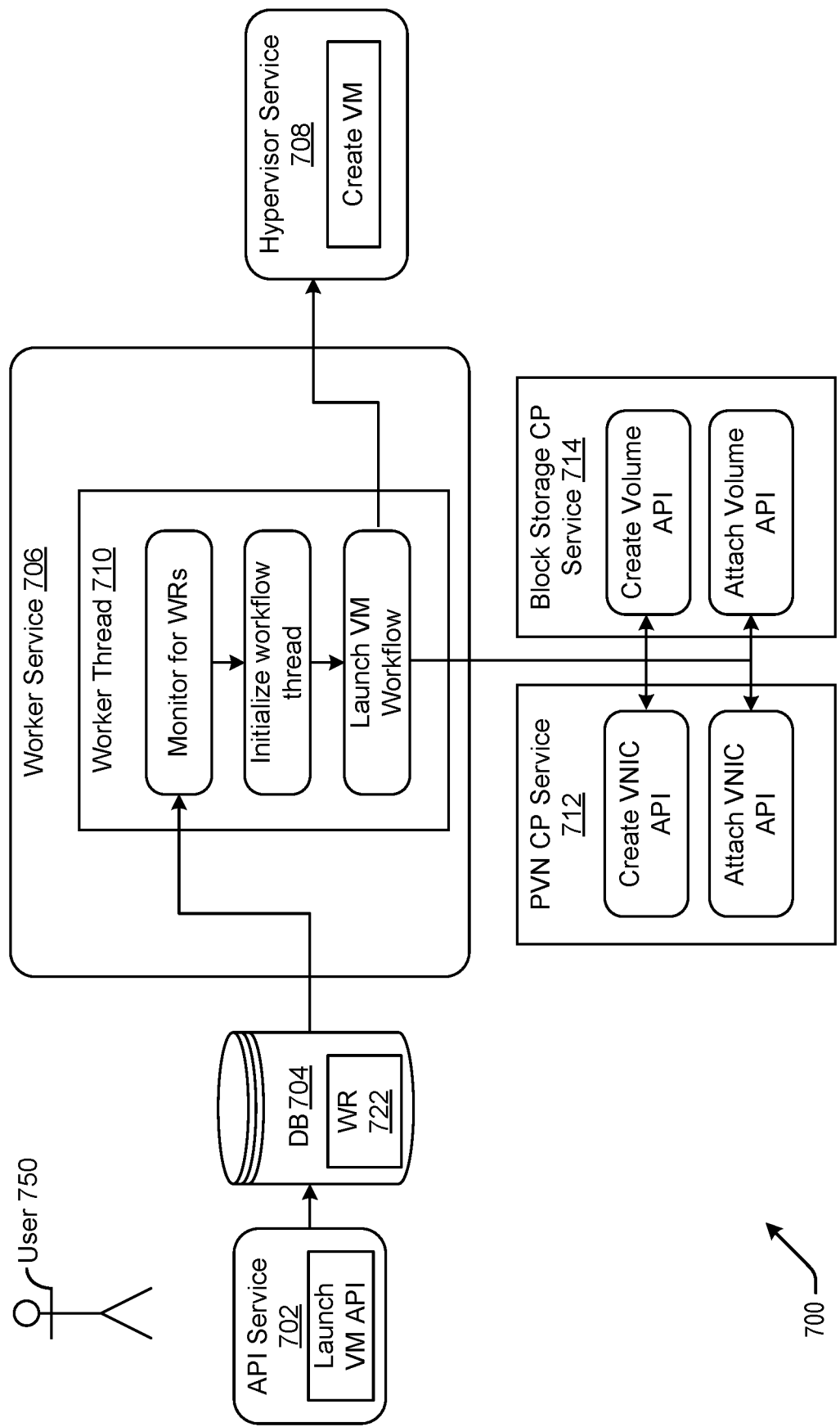
FIG. 7 is a block diagram depicting a control plane and flow for executing a workflow by one or more components of a cloud infrastructure edge computing device, according to at least one embodiment.

FIG. 7 is a block diagram depicting a flow 700 for executing a workflow by one or more components of a cloud infrastructure edge computing device, according to at least one embodiment. Components that execute the flow 700 may include API service 702, database 704, worker service 706, hypervisor service 708, PVN CP service, Block storage CP service 714, although more or fewer services may be included. In some embodiments, each of the services of FIG. 7 are an example of a service of the service(s) 502 of FIG. 5. In some embodiments, at least some of the functionality discussed in connection with the services of FIG. 7 may be combined in any suitable combination and provided as a single service or instances of the same service. By way of example, in some embodiments, the functionality of services 702-708 may be provided by a single service (e.g., compute CP service discussed above in connection with FIG. 5). In some embodiments, the functionality provided by the services 702-708 may be provided by a single edge device (e.g., edge device 500 of FIG. 5) or by two or more edge devices (e.g., by edge device 602 and edge device 604 of FIG. 6).

In some embodiments, the API service 702 may be configured to accept work requests that include intended state data that describes an intended state of a set of data plane resources (e.g., VM(s) 508 of FIG. 5). As a non-limiting example, user 720 may utilize a user device (e.g., the user device 202 of FIG. 2) to access a user interface with which he can make various selections indicating a desire to launch a VM. The user input may be received by the API service 702 (an example of the compute CP service of FIG. 5) which may generate a work request (e.g., WR 722) and utilize a predefined Launch VM API to store the work request in a distributed database (e.g., DB 704). In some embodiments, the DB 704 may be a computing cluster which is configured to use etcd3 as an immediately consistent, highly-available, transactional, distributed database. Generally, a work request indicates a desire and information needed to create and/or modify data plane resources such as VM(s) 508. In some embodiments, the work request includes state information indicating a desired state for the data plane resource. In some embodiments, the DB 704 may be accessible to all services operating on any edge device (and by services operating on any suitable edge device of an edge device cluster such as distributed computing cluster 600).

Worker service 706 (e.g., also an example of the compute CP service of FIG. 5) may be configured to execute one or more worker processes (e.g., computing thread 710). Some of these worker processes may be configured by the worker service 706 at any suitable time to execute a continuous and/or ongoing predefined workflow. By way of example, the worker service 706 may configure one or more worker threads (e.g., including computing thread 710) to monitor the DB 704 for new work requests (e.g., WR 722). The computing thread 710 may be configured to determine if a work request WR 722 is already being attended to. In some embodiments, this entails checking a predefined storage bucket within DB 704 for a unique identifier associated with WR 722. If the unique ID included within WR 722 does not appear in the bucket (or the WR is otherwise indicated as having not been picked up for processing), the computing thread 710 (e.g., a nanny thread) may initialize a workflow thread (e.g., another instance of a computing thread 710) which may then be configured by the computing thread 710 to execute a workflow corresponding to launching a VM corresponding to the WR 722.

The initialized workflow thread may be communicatively coupled (e.g., via the substrate network 502 of FIG. 5) to a workflow service (not depicted). The workflow service may be configured to identify, from one or more predefined workflows, one that corresponds to launching a VM, and therefore, to the work request 722. These predefined workflows identify one or more steps/operations to be taken, and a sequence to those steps, in order to achieve a predefined goal (e.g., launching a virtual machine, stopping/starting a virtual machine, terminating a virtual machine, creating a block volume, removing a block volume, etc.). The workflow thread may launch the VM workflow and oversee its execution by various other entities. In some embodiments, the workflow thread may pass any suitable portion of the intended state data of the DP resource to any suitable combination of services.

As a non-limiting example, as part of the workflow for launching a virtual machine (e.g., a VM to be hosted by hypervisor service 708), one or more APIs can be called for creating and attaching the VNIC. Similarly, a number of APIs may be provided for creating and/or attaching a block storage volume API. In some embodiments, the workflow thread may perform any suitable call to one or more APIs to invoke the functionality of PVN CP Service 712, which in turn may be configured to create and attach a VNIC. The workflow thread may then call block storage CP service 714 which may then execute any suitable operations to create and attach a block storage volume. The worker thread overseeing the workflow may ensure a designated order (e.g., create the VNIC first before creating the block volume). This worker thread may be configured to catch any errors and/or exceptions from one or more services it has invoked. If no exceptions/errors are encountered, the worker thread overseeing the workflow can provide any suitable data to the hypervisor service 708 (via the substrate network), which in turn, execute functionality for creating the VM requested. The hypervisor service 708 may provide actual state data for the newly launched VM. In some embodiments, the worker thread overseeing the workflow can store the actual state data in the DB 704 for later reference (e.g., when a monitor may determine whether the actual state data matches the requested state data indicating no changes needed or when the actual state data fails to match the requested state data, indicating a change of the data plane resources is needed).

In some embodiments, the workflow thread may be communicatively coupled to a cluster manager (not depicted). Cluster manager may be configured to manage any suitable number of computing clusters. In some embodiments, the cluster manager may be configured to manage any suitable type of computing cluster (e.g., a Kubernetes cluster, a set of computing nodes used to execute containerized applications, etc.). The workflow thread may be configured to execute any suitable operations to cause the cluster manager to execute any suitable orchestration operation on the DP resource(s) (e.g., a VM) in accordance with the instructions identified to bring the DP resource(s) in line with the intended state data. In some embodiments, a monitoring entity (e.g., the workflow thread, a thread launched by the workflow thread) may be communicatively coupled to DP resource(s) 116 and configured to monitor the health of DP resource(s). In some embodiments, the monitoring entity may be configured to store any suitable health data in the DB 704.

The specific operations and services discussed in connection with FIG. 7 is illustrative in nature and is not intended to limit the scope of this disclosure. The particular operations performed and services utilized may vary depending on the particular workflow associated with the requested operations.

In some embodiments of the present disclosure, techniques are disclosed for migrating one or more services from an edge device to a cloud computing environment. The edge device may be similar to edge device 100 of FIG. 1 and/or other edge devices described herein. In some embodiments, the edge device may execute within an isolated computing environment that is separate from the cloud computing environment that provides a plurality of services for executing customer workloads. Meanwhile, the cloud computing environment may be implemented by one or more data centers (e.g., on-premise and/or via a centralized cloud computing infrastructure). The phrase "migrating a service" is intended to include migrating resources such as virtual machine instances ("instances"), workloads, state data, metadata, or any suitable data and/or component associated with and/or utilized by a service.

In some embodiments, a migration service (e.g., associated with the cloud computing environment) may facilitate (e.g., coordinate) the migration process by performing one or more operations. For example, the migration service may identify a suitable computing device (or computing devices) of the cloud computing environment with a hardware profile that matches the edge device, and thus, is determined to be operable for executing services currently executed by the edge device. In some embodiments, the computing device may be one of a plurality of devices of the cloud computing environment. The migration service may further configure a virtual bootstrap environment (e.g., initially including an OS and/or a core set of services) of a dedicated region (e.g., dedicated for a particular customer) at the computing device (s) and then establish a communication channel (e.g., over a VPN) between the edge device and the computing device(s). The migration service may then execute a set of migration operations, including causing resources (e.g., instances, workloads, state data, metadata, and/or resource data) associated with one or more services, executing on the edge device, to be migrated to the computing device(s). Upon the completion of the migration process, the one or more services may execute within the cloud computing environment such that they accept traffic that was previously destined for the edge device. In some embodiments, the entities of the migrated services (e.g., identifiers, attributes, policies, etc.) may retain a similar (e.g., same) identity that was associated with their previous execution on the edge device. By facilitating this migration process, techniques herein enable, among other things, an efficient mechanism for customers to scale up service (and/or workload) deployments from an edge device(s) to a cloud computing environment (e.g., which may provide a more permanent, stable, and/or computing resource-equipped workload execution mechanism).

To further illustrate, consider a scenario in which a cloud services provider (CSP) provides a service to one or more customers, for example, including an organization (e.g., a healthcare organization) that operates in one or more remote regions of the world. In this example, the healthcare organization may have previously deployed an edge device(s) to a particular remote region. For example, the organization may be intending to build (and/or provision) a permanent facility (e.g., a data center) at the remote region where they are establishing a new place of operation. In some embodiments, one or more services of the data center may be associated with (and/or provisioned by) the CSP, for example, to enable an on-premise cloud computing environment for the organization. In some embodiments, the data center (and/or edge device) may (or may not) be connected to a centralized cloud computing environment of the CSP (e.g., not located on-premise nor at the remote region). In this example, while the data center is being prepared (e.g., constructed and/or otherwise provisioned with resources to enable an on-premise cloud computing environment), the organization may still want to execute computing workloads, for example, to collect, analyze, and/or store patient health data in the remote region. Thus, the organization may have previously deployed the edge device to execute workloads at least on a temporary basis, until the data center is operational.

Suppose that, upon the data center being made operational (e.g., provisioned to operate with a set of cloud computing environment services of the CSP), the healthcare organization wants to migrate currently executing services (that utilize resource instances, databases, workloads, etc.) from the edge device to data center that is implementing the cloud computing environment. For example, as described herein, the healthcare organization may want to scale up the workloads currently executing on the edge devices (e.g., to a more permanent environment and/or having more computing resources available to process additional workloads). It should be understood that, although in this example, the cloud computing environment may be provided via an on-premise customer data center, embodiments should not be construed to be so limited. For example, in another scenario, the healthcare organization may want to migrate currently executing services from the edge devices to the centralized cloud computing environment of the CSP. By way of example, the healthcare organization may execute at the edge device a number of services (e.g., a database-as-a-service service that manages a database instance, a machine-learning service that manages an automated intelligence classifier, etc.). The healthcare organization may wish to migrate resources (e.g., the database instance an its contained data, the trained machine-learning classifier and/or the associated training data used to train the ML classifier, etc.). It should be understood that the service migration techniques described herein may be applicable with respect to migration from one or more edge devices to any suitable cloud computing environment.

Continuing with the above illustration, a computer system of the cloud computing environment may receive a request from a user device of the customer to migrate the one or more services (and/or associated resources) from the currently deployed edge device to the cloud computing environment of the data center. The computer system may execute a migration service to execute (and/or facilitate execution of) one or more operations to perform the migration process. For example, as described herein, the migration service may identify particular computing device(s) associated with a dedicated region (e.g., a newly provisioned dedicated region or an existing dedicated region) of the cloud computing environment. In this example, the dedicated region may include hardware and/or software computing resources of the on-premise data center that have been provisioned by the CSP to operate as a cloud computing environment (e.g., executing services provided and/or managed by the CSP). In some embodiments, the dedicated region (e.g., hardware and/or software of the dedicated region) may be configured (e.g., via policy settings, metadata, etc.) to be associated with (e.g., assigned to) a particular namespace (e.g., which may further be associated with the particular identity, a particular region, and/or any suitable identifiers/attributes). In another example, the dedicated region may include a portion (e.g., subset) of computing resources of the centralized cloud computing environment of the CSP that is provisioned to the particular customer. Continuing with this example, the migration service may determine that a first hardware profile (e.g., indicating a CPU, memory, GPU, and/or other hardware capabilities) of the particular computing device of the dedicated region matches a second hardware profile of the edge device. This matching process may be performed in part to verify that the particular computing device is suitable (e.g., has sufficient resources) for executing a service that is migrated from the edge device to the cloud computing environment.

The migration service may then configure, at the computing device, a virtual bootstrap environment of the dedicated region. The virtual bootstrap environment may be configured in part by initially provisioning (e.g., imaging) the computing device with an OS and a core set of services. The core set of services may correspond to one or more services (e.g., network services, storage services, etc.) that are pre-requisite services for installing additional services of the virtual bootstrap environment. The core set of services may further enable a first set of services, associated with the edge device, to be successfully migrated to the dedicated region and executed as a second set of services. The second set of services of the dedicated region may be a subset of the full set of services determined to be deployed to the dedicated region and may further correspond to the first set of services to be migrated from the edge device. It should be understood that the dedicated region may also be provisioned to execute other one or more services (e.g., of the full set of services to be deployed) that do not have corresponding service (e.g., a counterpart) executing on the edge device. Upon identifying the computing device as being a suitable match and provisioning the computing device with core services (e.g., including a VPN service), the migration service may cause a communication channel to be established (e.g., over a VPN) between the edge device and the computing device.

To further facilitate configuring the virtual bootstrap environment, the migration service may determine an ordering in which to migrate resources and/or launch services in the dedicated region (e.g., a topological sort ordering based on a directed acyclic graph (DAG) of service dependencies). With respect to a particular service that is identified (e.g., based on the DAG of service dependencies) as a next service to be deployed (e.g., within the dedicated region), the migration service may first determine if there is a counterpart service executing on the edge device (e.g., one of the first set of services to be migrated). If not, the particular service may be deployed following a predefined (e.g., non-migration) protocol for launching services, which may correspond to typical installation process for a cloud computing service. If yes, the particular service may be deployed by following a particular migration protocol, which may include performing a set of migration operations. In one example, the migration service may cause the dedicated region to initialize (e.g., with an initial set of attributes, identifiers, etc.) the particular service as being one of the second set of services, as described above. The set of migration operations may further include one or more other suitable operations, for example, including ensuring that the initialized service is ready to accept migrations from the counterpart service on the edge device, configuring the counterpart service to disable resource mutations (e.g., transitioning the service to a read-only mode), capturing a state of the service (e.g., from the perspective of the edge device), migrating service metadata from the edge device to the dedicated region counterpart service, migrating resource data (e.g., files, data objects, etc.) associated with the service, enabling the dedicated region service to accept all traffic previously destined for the edge device counterpart service, validating that the service state was successfully migrated (e.g., based on capturing (and/or comparing) state data for both the dedicated region service and the edge device counterpart service), shutting down the counterpart service on the edge device, etc. The migration service may execute any suitable number and/or type of migration operations such that the first set of services of the edge device is successfully migrated to be executed as the second set of services of the dedicated region.

In some embodiments, while executing the set of migration operations (e.g., to migrate a particular service and/or associated resources), the migration service may cause at least a portion of default configuration data of the virtual bootstrap environment (e.g., including metadata associated with a counterpart initialized service of the dedicated region) to be adjusted to match service metadata for the particular service that is migrated from the edge device to the dedicated region. In this way, the migrated services (e.g., executing in the dedicated region as the second set of services) may be configured to execute with the same identity as the first set of services previously executing on the edge device. This may, for example, ensure a continuity of service operations post-migration, when the newly migrated service is enabled to accept all traffic previously destined for the original particular service on the edge device.

In some embodiments, data associated with a particular service may be migrated according to one or more migration protocols for the particular service. For example, in one case, a particular migration protocol may indicate that resources associated with the services are to be copied to the initialized service of the dedicated region. In another case, the particular migration protocol may indicate that the migration service is to use an API (e.g., of the initialized service of the dedicated region and/or the counterpart service being migrated) to migrate the resource(s). In some embodiments, the API may be used to reconstruct an object being migrated and/or ensure that resource is associated with the correct metadata. It should be understood that any suitable migration protocol(s) may be used to migrate resources for a particular one or more services.

Continuing with the illustration above, in this example, upon confirming that the first set of services (and/or corresponding resources) have been successfully migrated to the dedicated region (e.g., such that the second set of services are configured to execute as the first set of services from within the dedicated region), the migration service may shut down the first set of services and/or shutdown (e.g., decommission the edge device). Note that, as described herein, this service migration process thus provides an efficient mechanism to migrate resources (e.g., workloads and/or state data) seamlessly into a dedicated region, thus enabling resources to operate and/or be utilized in a more permanent, scalable deployment.

In some embodiments, services of any suitable number of edge devices may be migrated to a dedicated region. For example, a plurality of edge devices may be configured to operate as a distributed computing cluster. In this example, the service migration process may involve migrating services (and/or corresponding resources) from each of the edge devices of the cluster to a particular dedicated region. In some embodiments, devices (and/or services) of a given cluster may be migrated to the same dedicated region based in part on the device of the cluster being associated with the same namespace (e.g., thus, avoiding identity and/or policy conflicts). In some embodiments, multiple clusters may be associated with the same (or different namespaces). In some embodiments, migrating more than one cluster to a new namespace (e.g., of a new dedicated region) may be performed based in part on resolving conflicting configuration data (e.g., conflicting policies) among the different clusters. In some embodiments, migration to an existing dedicated region (e.g., associated with its own existing namespace) may be possible upon ensuring that potential conflicts are resolved. In general, the particular migration procedure (e.g., conflict resolution protocol) employed may depend on any one or more factors, including, for example, a number of clusters being migrated, whether the clusters are associated with different (or the same) namespaces, whether the target dedicated region is an existing dedicated region or a new dedicated region, whether policies across different namespaces conflict, whether conflicting policies may be resolved within the same namespace, etc. In some embodiments, the one or more migration protocols may be predefined protocols (e.g., predefined for a particular service type, a particular environment in which the cluster operations, etc.) that enable migration to be performed automatically, including automatic resolution of conflicts. In some embodiments, the protocol may include requesting for manual input (e.g., from a customer agent) to resolve a conflict. In some embodiments, a full sequence of operations to be performed by the migration can be generated and provided to a user for approval prior to starting/continuing the bootstrap and/or migration process.

Embodiments of the present disclosure provide several technical advantages over conventional systems. For example, as described herein, customers may want to offload computing tasks from a centralized cloud computing environment to a disconnected region (e.g., utilizing one or more edge devices). In some cases, the edge device deployments may be temporary, whereby a customer intends to scale up the workloads once an on-premise cloud computing environment (e.g., a private cloud) becomes available. Embodiments described herein facilitate an efficient process to automatically migrate workloads and state seamlessly to a cloud computing environment such that the workloads may continue to execute in a more permanent and/or scalable deployment. Correspondingly, customers may be more willing to use edge devices for initial deployments at least in part because of the available option for migrating services from those edge devices if/when the customer wants to scale up.

For clarity of illustration, embodiments are described herein primarily with respect to migrating one or more services (and/or corresponding resources) from an edge device (and/or cluster of devices) to a cloud computing environment (e.g., a dedicated region of the cloud computing environment). However, embodiments should not be construed to be so limited. For example, techniques may be applicable to any suitable migration process that migrates one or more services (and/or corresponding resources) from a first computing device to a second computing device, whereby resolution of namespace-related conflicts (e.g., identity conflict resolution, policy conflict resolution, etc.) may be performed (e.g., automatically) during the migration. In one example, a service (and/or corresponding resources) may be migrated from an on-premise private cloud (e.g., a dedicated region of a CSP located at a customer data center) to a centralized cloud computing environment of the CSP (and/or vice versa).

Figure 8:
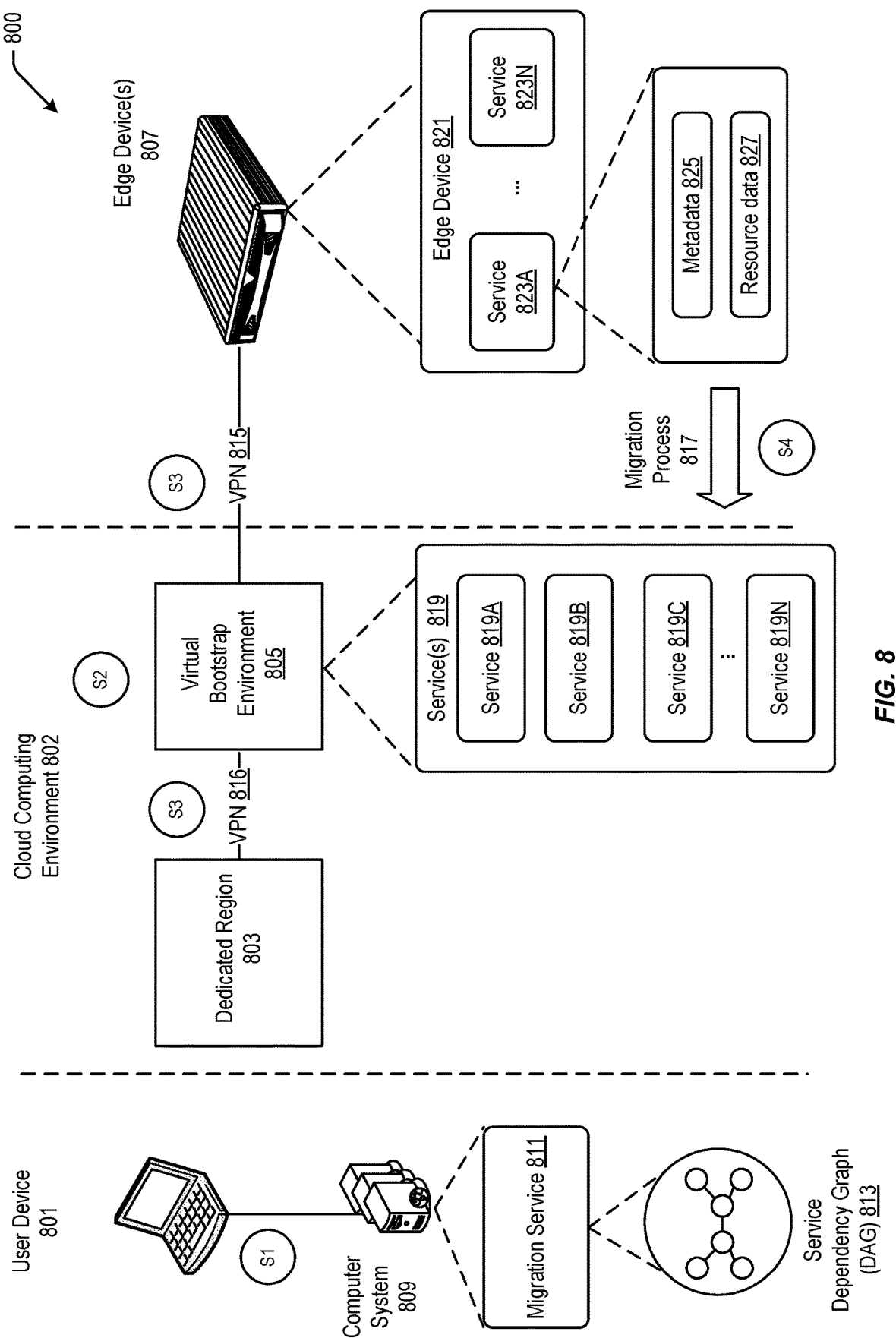
FIG. 8 is a block diagram illustrating an example environment for migrating a service from one or more edge devices to a cloud computing environment, according to some embodiments.

FIG. 8 is a block diagram illustrating an example environment 800 for migrating a service (and/or resources) from one or more edge devices to a cloud computing environment 802 (e.g., to a dedicated region 803 of the cloud computing environment, in some instances, via the virtual bootstrap environment 805), according to some embodiments. In FIG. 8, several elements are depicted, including user device 801 (e.g., a laptop, PC, etc.), computer system 809 (e.g., a server device), dedicated region 803 of a cloud computing environment 802, and edge device(s) 807 (e.g., which may correspond to any of the edge devices described in reference to FIGS. 1-7). In the illustration of FIG. 8, computer system 809 and/or the dedicated region 803 of the cloud computing environment may be associated with (e.g., managed by) a cloud services provider. The dedicated region 803 may be associated with (e.g., and/or be implemented by) one or more computing devices, as described further herein.

As described further herein, the elements of FIG. 8 are depicted in association with performance of one or more operations of a migration process. For example, at step S1 of FIG. 8, a migration service 811 of computer system 809 may receive a request (e.g., from user device 801, which may be associated with a particular customer of a CSP) to migrate one or more services (and/or associated resources such as virtual machine instances ("instances," for brevity), workloads, state data, metadata, or the like) that are currently deployed to (e.g., executing on) one or more edge device(s) 807. In any of the examples provided herein, any reference to migrating one or more services can equally apply to migrating resources such as instances, workloads, state data, metadata, etc. irrespective of whether such resources are service related. The edge device(s) 807 may currently be provisioned to the particular customer for use in executing customer workloads via one or more services. Using edge device 821 as a representative example of the one or more edge device(s) 807, edge device 821 may execute one or more services (e.g., service 823A-823N). In some embodiments, a service (e.g., service 823A, being a representative service) may be associated with, among other data elements/ resources, service metadata 825 (e.g., including policy settings, access controls, etc.) and resource data 827 (e.g., including files, folders, and/or other data objects). In some embodiments, a service may be configured to execute any suitable computing workloads (e.g., hosting a web server to process web traffic, executing a machine learning algorithm to analyze data, storing customer data records, etc.). In some embodiments, a particular edge device (e.g., edge device 821) may be associated with a particular hardware profile. For example, a hardware profile may indicate a number of CPU cores (e.g., 40 CPU cores) and/or a number of memory units (e.g., 512 Gigabytes). It should be understood that any suitable features may be associated with a hardware profile, including, but not limited to, CPU resources, memory resources, data bus types, disk storage types, network card types, other processor types (e.g., GPU resource), etc. A particular hardware profile of an edge device may enable the edge device to process data in accordance with workload requirements. For example, a particular processor unit type may enable efficient processing of data (e.g., images, video, etc.) by the edge device.

As described above, in some embodiments, edge device(s) 807 may include a plurality of edge devices. The plurality of edge devices may be collectively configured to operate as a distributed computing cluster (e.g., connected together over a VPN), for example, similar to distributed computing cluster 600. In some embodiments, the distributed computing cluster may be used to execute an increased number of workloads among the devices of the cluster. In some embodiments, one or more services may be executed by each edge device to execute the workloads, and the services may (or may not) coordinate with each other.

In some embodiments, an edge device (and/or cluster of edge devices) may be associated with (e.g., belong to) a particular namespace. In some embodiments, a namespace may indicate a taxonomy for configuration data identities such that, for a particular namespace the identities are unique within the particular namespace. In some embodiments, the namespace may further be associated with (e.g., and/or provide a taxonomy for) any suitable data objects (e.g., VMs, files, etc.), relationships between objects, policies, resource data, attributes, identifiers, and the like, within the namespace.

In some embodiments, upon receiving the request to migrate services (and/or resources) from the edge device(s) 807, the migration service 811 may obtain (e.g., access) a manifest file associated with the edge device. The manifest file may identify information associated with the edge device(s) 807 that may be used by the migration service 811 to determine instructions for coordinating the service migration process. For example, as described further below, the manifest file may indicate a hardware profile of the one or more edge device(s) 807. In some embodiments, the manifest file may indicate a list of services (e.g., an inventory list) that are currently deployed to the edge device(s) 807 (e.g., indicating services deployed per edge device) that are requested for migration. It should be understood that any suitable information about the edge device(s) 807 may be obtained to coordinate the migration process. The information may be obtained at any suitable time(s) during the service migration process (e.g., upon receiving the request, after provisioning a new dedicated region (described further below), etc.).

At step S2, the migration service 811 may identify that a first hardware profile associated with dedicated region 803 matches a second hardware profile of edge device(s) 807 (e.g., in this example, including at least edge device 821). For example, the migration service 811 may identify one or more particular computing device(s) (not depicted) of a cloud computing environment 802. As described herein, in one example, the cloud computing environment may be associated with a data center of the customer, whereby at least a portion of the computing resources of the data center are managed by the CSP. In another example, the cloud computing environment may be associated with a centralized cloud computing environment managed by the CSP. In any case, the migration service 811 may identify, for example, that the second hardware profile of edge device 821 matches a first hardware profile of the particular computing device (e.g., having a similar number of CPU cores, similar processor types, etc.), and thus, is a suitable candidate for receiving migrated services from the edge device 821. In general, it should be understood that the cloud computing environment 802 may include (and/or be implemented by) a plurality of computing devices, which may (or may not) be located at one or more data centers (e.g., in different geographic regions). The devices may correspond to servers, server clusters, racks, and the like. In some embodiments, the devices may be networked together and accessible via one or more networks (e.g., the Internet, a VPN, etc.).

As described above, the particular computing device (not depicted) may be associated with dedicated region 803, which may be a newly provisioned (or existing) dedicated region. In some embodiments, the dedicated region 803 may be associated with hardware and/or software computing resources (e.g., including the particular computing device) that have been provisioned for the particular customer. In some embodiments, a new dedicated region of the cloud computing environment may be provisioned upon receiving the request from user device 801 to migrate services from the edge device(s) 807 to the cloud computing environment. For example, the migration service 811 may identify the particular computing device as a having a suitable hardware profile match, and then may provision dedicated region 803 as a new dedicated region in association with at least the particular computing device. In some embodiments, the migration service 811 may determine to migrate the services to an existing dedicated region, which may be associated with the particular computing device. It should be understood that one or more computing devices (e.g., each device having a respective hardware profile) may be associated with a given dedicated region. In some embodiments, the dedicated region 803 may be associated with a particular namespace. Similar to as described with respect to the namespace for edge device(s) 807, the namespace for dedicated region 803 may indicate a taxonomy for data identities (and/or relationships thereof) within the dedicated region 803. In some embodiments, the namespace (e.g., including namespace elements) for the dedicated region 803 may be different from the namespace associated with the edge device(s) 807.

Continuing with step S2, upon a identifying a dedicated region with a suitable hardware profile (e.g., suitable computing resources of a computing device(s)), the migration service 811 may configure a virtual bootstrap environment 805 (provided by the same or different computing device(s) as the dedicated region 803). In some embodiments, the virtual bootstrap environment 805 may include an OS and one or more core services. In some embodiments, the core services may include a set of services that is a subset of the full set of services available within the cloud computing environment. This core set of services may be determined (e.g., by an administrator) to be sufficient to facilitate performing a migration process 817 between the edge device(s) 807 and the dedicated region 803. In one example, core services may include networking services (e.g., to facilitate setting up a communication channel between the edge device(s) 807 and the dedicated region 803), disk storage services, device management services, etc. Any suitable number and/or type of services and/or resources may be deployed to configure the virtual bootstrap environment 805. The core services of the virtual bootstrap environment 805 may correspond to at least a subset (e.g., including 819A-819B, etc.) of the full set of service(s) 819 (e.g., including 819A-819N) that will eventually be deployed to the dedicated region 803 upon completion of the migration process 817. For example, as described further herein, at least a portion (e.g., some or all) of services 823A-823N (and/or corresponding resources) may subsequently be migrated to the dedicated region 803 and deployed as services 819C-819N of service(s) 819 (e.g., corresponding to services running in addition to the core set of services). As described further below, regarding services/resources that are to be deployed to the dedicated region 803 that have a counterpart service on an edge device (e.g., edge device 821), the migration process may include first deploying an initial (e.g., new) service in the dedicated region 803, and then migrating the counterpart service so that the new service is configured to execute as the counterpart service. In some embodiments, one or more of the service(s) 819 may not be associated with a counterpart service on an edge device. For example, the cloud computing environment at the data center may include some services (e.g., executing one or more machine learning algorithms) that are not deployed to edge devices. In some embodiments, these services may also be deployed to the dedicated region 803 (e.g., as part of and/or subsequent to configuring the virtual bootstrap environment 805).

At step S3, the migration service 811 may establish a communication channel between the edge device 821 (e.g., being representative of the edge device(s) 807 to be migrated) and the computing device configured with the virtual bootstrap environment 805. For example, the migration service 811 may initiate a process by which the communication channel (e.g., VPN 815) is established between the computing device(s) implemented the virtual bootstrap environment 805 and the edge device 821. Likewise, the migration service 811 may initiate a process by which another communication channel (e.g., VPN 816) is established between the computing device(s) implementing the dedicated region 803 and the computing device(s) implementing the virtual bootstrap environment 805. Although not depicted in FIG. 8, in some embodiments, the migration service 811 may initiate a process by which a communication channel (e.g., a VPN) may be established between the dedicated region 803 and the edge device(s) 807 such that the migration process 817 may be executed between the edge device(s) 807 and dedicated region 803, directly, without utilizing the virtual bootstrap environment 805. In one example, the migration service 811 may transmit a message to edge device 821 with an address for contacting a computing device (e.g., a computing device of the virtual bootstrap environment 805 or the dedicated region 803) to set up the communication channel with the computing device. It should be understood that the communication channels discussed above may utilize any suitable one or more networks and/or mediums (e.g., the Internet, a private network, a WiFi network, Ethernet, etc.). In some embodiments, a different communication channel may be established between the virtual bootstrap environment and each of the edge device(s) 807 being migrated. In some embodiments, multiple virtual bootstrap environments may be utilized (e.g., one for each edge device of edge device(s) 807). Likewise, multiple dedicated regions may be utilized with corresponding communication channels between corresponding virtual bootstrap environment and the multiple dedicated regions.

At step S4, the migration service 811 may execute a set of migration operations to coordinate the migration process 817 between edge device 821 and virtual bootstrap environment 805 (e.g., over the VPN 815). For example, as described further herein (e.g., with respect to FIG. 9), the migration service 811 may generate a service dependency graph 813 that indicates an ordering of services that are to be eventually deployed to the dedicated region. In some embodiments, the dependency graph 813 may include a directed acyclic graph (DAG) of service dependencies. In some embodiments, as described above, the dependency graph may (or may not) include one or more of the core set of services of the virtual bootstrap environment 805. In some embodiments, the dependency graph may include nodes for services that have a counterpart service on an edge device being migrated (e.g., the first set of services). The dependency graph may further include nodes for additional services that do not have a counterpart service being migrated. In this way, the migration service 811 may ensure that each service is ready to be deployed at the appropriate time/order (e.g., when other dependent services have been deployed). In some embodiments, the DAG may (or may not) differentiate between services that are being migrated and those that do not have a migrating counterpart. In some embodiments, the information used to generated the DAG may be obtained from one or more sources. For example, a configuration file (e.g., a Terraform configuration file) may be determined (e.g., predetermined) by the migration service 811 that identifies a list of services (e.g., which may indicate service definitions, associated resources files, etc.) that will be launched by the computing device of the dedicated region 803 (e.g., including at least a subset of services provided by the cloud computing service). In some embodiments, the DAG may (or may not) be generated based in part on a manifest file received from the edge device 821 (e.g., indicating what services are to be migrated).

In some embodiments, following the generation of the dependency graph, the set of migration operations may include facilitating a migration of each service of the first set of services (and/or corresponding resources). For example, as described with reference to FIGS. 9 and 10, the migration service 811 may iterate through each service (and/or resource) according to the dependency graph 813 until all of the first set of services (and/or corresponding resources) have been migrated. Each service (and/or resource) may be first migrated to the virtual bootstrap environment 805 before being migrated to the dedicated region 803. In some embodiments, a validation process may be performed upon migrating services/resources to the virtual bootstrap environment 805 before migrating the services/resources to the dedicated region 803. Upon completion of the migration process 817 the dedicated region 803 of the cloud computing environment may be enabled to execute a second set of services that respectively corresponds to the successfully migrated first set of services. As described above, it should be understood that the second set of services (e.g., corresponding to the migrated first set of services) may be a subset of the full set of services deployed and configured to execute in the dedicated region 803 (e.g., using the virtual bootstrap environment 805). In some embodiments, the second set of services may correspond to any suitable cloud computing services that are determined to be deployed to the dedicated region and which also have a counterpart service that executes on the edge device being migrated. In some embodiments, a validation process may be performed upon completion of the migration process 817 (and/or each service migration), to ensure that each service has been successfully migrated. Upon completing the end-to-end validation process, the migration service 811 may perform any suitable actions. For example, the migration service 811 may cause the respective edge device (e.g., edge device 821) to be shut-down (and/or decommissioned) (e.g., through transmission of a command to shut down). In some embodiments, the migration service 811 may shut down a particular service (e.g., one of the first set of services) on the edge device 821 (e.g., via transmission of a command to shut down that particular service), once the service is confirmed to be successfully migrated to the dedicated region 803 (e.g., executed as one of the second set of services).

Although the computing device of the dedicated region 803 was described above with respect to a single computing device, it should be understood that the dedicated region 803 may be implemented by any suitable number of computing devices (e.g., a server cluster). The one or more computing devices may be similar (e.g., the same) or different, depending, for example, on hardware profile requirements (e.g., identified in part via the hardware profile of the edge device(s) 807).

Also, as described herein, the edge device(s) 807 may include a cluster of edge devices (e.g., a distributed computing cluster). In some embodiments, migration process 817 may involve performing a migration process for each edge device (e.g., over respective VPN channels). In some embodiments, the services executing in a distributed computing cluster may be associated with a particular namespace (e.g., a first namespace). The first namespace may indicate identities (e.g., unique identities) and/or relationships between data (e.g., including files, identifiers, attributes, policies, etc.) associated with the first namespace. In some embodiments, each of the services operating within the first namespace of the given cluster may be migrated to a particular dedicated region, which may be associated with its own namespace (e.g., a second namespace). As described further herein, one or more migration operations may be executed (e.g., and/or coordinated) by the migration service 811 to ensure that the identities and/or relationships (e.g., between data and/or policies) of the first namespace are preserved when migrated to the second namespace. The migration operations may include migrating any suitable resource (e.g., resources corresponding to a service such as instances, workloads, state data, metadata, etc.) and modifying configuration data of the dedicated region such that identities and/or relationships (e.g., among data and/or policies) of the first namespace are preserved. In this way, the second set of services may be configured to execute as the first set of services within the dedicated region 803 of the cloud computing environment. Furthermore, the second set of services may be configured to accept all traffic previously destined for the edge devices.

In some embodiments, and, as described further herein, the migration process 817 may involve migrating any suitable number of clusters (e.g., each cluster including one or more edge devices) to one or more dedicated regions. The operations of the migration process 817 may depend on, for example, whether a plurality of clusters being migrated are collectively associated with the same or different namespace, whether the plurality of clusters are being respectively migrated to different dedicated regions (e.g., each having a different namespace) or to the same dedicated region, whether there are conflicting policies between the different clusters, whether the target dedicated region is an existing dedicated region or was newly provisioned for the particular migration process, etc. In some embodiments, a different migration protocol may be employed, depending on the particular context. The particular protocol(s) employed may ensure that the resulting configuration (e.g., executed in the dedicated region 803) preserves identity information (e.g., associated with service data, such as metadata and/or resource data) and resolves identity (and/or policy) conflicts such that the migrated services effectively may resume operation under a similar configuration (e.g., including customer-visible policies) as existed when operated by the edge cluster(s).

Figure 9:
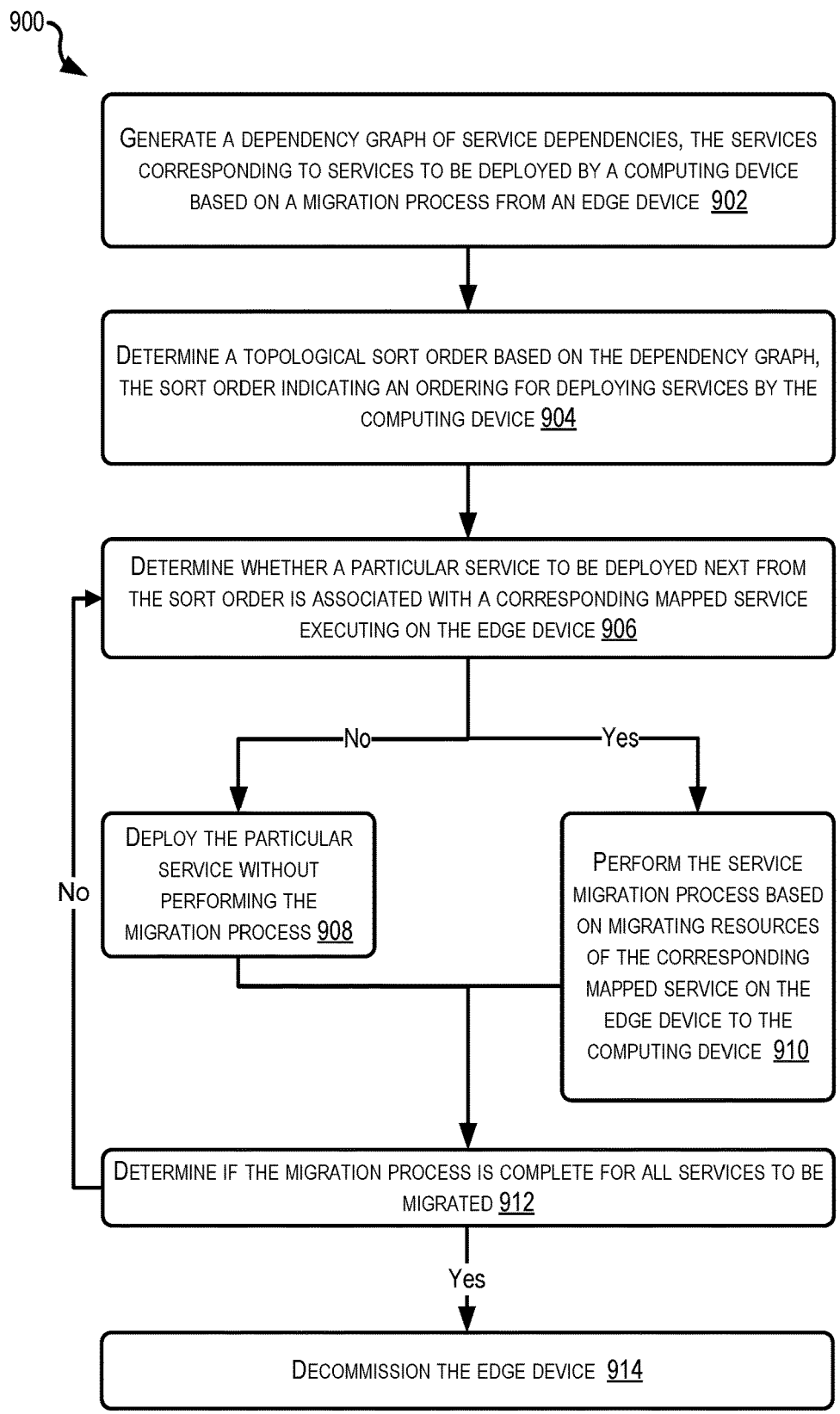
FIG. 9 is a flow diagram illustrating an example technique for facilitating a migration of one or more services from an edge device to a cloud computing environment, according to some embodiments.

FIG. 9 is a flow diagram illustrating a process 900 for facilitating a migration of one or more services (and/or corresponding resources) from an edge device to a cloud computing environment, according to some embodiments. One or more of the operations of the blocks of process 900 may correspond to the migration process 817 of FIG. 1. In some embodiments, process 900 may be performed by any suitable computing device associated with a cloud computing environment (e.g., migration service 811 of computer system 809 of FIG. 1). In some embodiments, process 900 may involve executing instructions that cause one or more devices (e.g., edge device(s) 807, a computing device of the virtual bootstrap environment 804, a computing device of the dedicated region 803, etc.) to further perform operations, for example, transmitting data between the devices.

Process 900 (and/or other processes described herein) is respectively illustrated as a logical flow diagram, each operation of which represents a sequence of operations that can be implemented in hardware, computer instructions, or a combination thereof. In the context of computer instructions, the operations represent computer-executable instructions stored on one or more computer-readable storage media that, when executed by one or more processors, perform the recited operations. Generally, computer-executable instructions include routines, programs, objects, components, data structures, and the like that perform particular functions or implement particular data types. The order in which the operations are described is not intended to be construed as a limitation, and any number of the described operations can be combined in any order and/or in parallel to implement the processes.

Additionally, some, any, or all of the processes may be performed under the control of one or more computer systems configured with executable instructions and may be implemented as code (e.g., executable instructions, one or more computer programs, or one or more applications) executing collectively on one or more processors, by hardware, or combinations thereof. As noted above, the code may be stored on a computer-readable storage medium, for example, in the form of a computer program comprising a plurality of instructions executable by one or more processors. The computer-readable storage medium is non-transitory.

Turning to process 900 in further detail, at block 902, a computer system (e.g., the computing devices of the virtual bootstrap environment 805, or other computing devices of the cloud computing environment 802) may generate a dependency graph of service dependencies, whereby the services correspond to services to be deployed by a computing device (e.g., the computing devices of the virtual bootstrap environment 805) based in part on a migration process from an edge device.

To generate the DAG, the computer system may identify a core set of services (e.g., a VPN service, a storage service, a memory management service, a Domain Name System (DNS) service, a Dynamic Host Configuration Protocol (DHCP) service, etc.) for initially configuring the virtual bootstrap environment. In some embodiments, the composition of the core set of services may (or may not) be dependent on the hardware profile of the corresponding edge device and/or the first set of services being migrated. For example, a particular service may be identified as being required for enabling a particular hardware device (e.g., a particular graphics processing unit (GPU)) of the computing device, the particular GPU being identified as matching a corresponding GPU of the edge device. Accordingly, the particular service may be included in the core set of services to be deployed to the dedicated region. In another example, one of the first set of services (or resources) being migrated (e.g., a database management service, a database instance and/or corresponding data managed by the database management service) may be identified as being dependent on a particular disk storage service. The particular disk storage service may thus be included in the core set of services to be deployed to the dedicated region.

At any suitable time, the set of services operating at the edge device(s) may be obtained (e.g., via the manifest discussed above) and a superset of the core services and the services to be migrated may be identified (e.g., from the manifest). Upon determining the full set of services to be deployed (e.g., the superset of services to be deployed to the virtual bootstrap environment 805), the computer system may generate the dependency graph based at least in part on resource definitions corresponding to each of the services of the superset. The dependency graph may be a directed acyclic graph (a DAG, such as DAG 813) of service dependencies. The DAG may indicate dependencies among the set of services being deployed.

At block 904, the computer system may determine a topological sort order based on the dependency graph, the sort order indicating an ordering for deploying services by the computing device to the dedicated region. The topological sort order may include a linear ordering of vertices of the dependency graph such that the computer system may identify an ordering for deploying (e.g., launching and/or migrating) services. Although a topological sort order (e.g., based on a DAG) is described herein as being used to determine an ordering for deploying services at the dedicated region, it should be understood that any suitable mechanism may be used to determine the ordering (e.g., a pre-defined ordering, based on a pre-defined list of services to be deployed).

At block 906, the computer system may determine whether a particular service to be deployed next from the sort order is associated with a corresponding mapped service executing on the edge device. For example, the computer system may reference the manifest file that was previously received, and determine whether the particular service is one of the services executing on the edge device that is a candidate for being migrated.

At block 908, upon determining that the particular service to be deployed next does not have a counterpart service on the edge device, the computer system may deploy the particular service without performing operations associated with the migration process (e.g., without migrating any resources). For example, suppose that the particular service in this case corresponds to a cloud computing service (e.g., offered by the CSP) that executes one or more machine learning algorithms. The computer system may deploy the service via any suitable one or more mechanisms (e.g., using a VM, a containerization mechanism, a file-copy, etc.).

At block 910, upon determining that the particular service to be deployed next does have a counterpart service on the edge device, the computer system may perform the migration process based on migrating resources (e.g., instances, workloads, state data, metadata, etc.) of the corresponding mapped service on the edge device to the computing device. For example, suppose that one of the cloud computing services supported by the cloud computing environment is a particular database management service. The database management service may be one of the set of services determined to be deployed to the dedicated region (via the virtual bootstrap environment 805). In this example, the database management service may also correspond to (e.g., be mapped to) a database management service executing on the edge device (e.g., as a matching/equivalent counterpart service). In this example, as described in further detail herein (e.g., with respect to FIGS. 10 and 11), the computer system may perform the migration process to migrate the counterpart service to the dedicated region. This may include initializing a new (e.g., blank) service in the virtual bootstrap environment 805 and then executing a protocol to accept data migration (e.g., including service metadata migration and/or resource data migration) to the new service. The data migration protocol may involve adjusting (e.g., updating) at least a portion of default configuration data of the initialized new service to match the service metadata migrated from the edge device. Thus, upon completion of the migration process for the particular service, the new service (e.g., one of the second set of services, described above) will be fully configured to execute in the virtual bootstrap environment 805 as the counterpart service (e.g., one of the first set of services) that was previously executing on the edge device.

At block 912, the computer system may determine if the service migration process is complete for all services to be migrated. For example, the computer system may reference the dependency graph (and/or the sort order) and determine if any other services are to be migrated (and/or deployed). If yes, then the process may loop back to block 906, whereby the next service to be migrated is determined. In some embodiments, this loop cycle may be performed until all services from the dependency graph are deployed to the virtual bootstrap environment 805 (e.g., including both services that were migrated and non-migrated services). In some embodiments, the completion of this deployment process may complete the deployment of the virtual bootstrap environment 805. In some embodiments, a validation process may be performed to validate the completion of the service migration process for all of the migrated services of the edge device being migrated. For example, the computer system may obtain first state data that corresponds to a current state of the first set of services associated with the edge device. The computer system may further obtain second state data that corresponds to a current state of the second set of services associated with the virtual bootstrap environment. The computer system may then compare the first state data with the second state data to validate that the current state of the second set of services matches the current state of the first set of services. In accordance with a determination of a successful validation, the computer system may repeat any suitable combination of the steps described at 902-912 and migrate the services (and/or corresponding resources) to the dedicated region 803 from the virtual bootstrap environment 805. If the migration from the virtual bootstrap environment 805 to the dedicated region 803 is successful (e.g., validated), the computer system of the cloud computing environment (e.g., the may configure the second set of services to accept traffic previously intended for the first set of services of the edge device. Alternatively, in accordance with a determination of an unsuccessful validation, the computer system may perform one or more remedial actions associated with correcting a mismatch between the second state data of the second set of services and the first state data of the first set of services. For example, the computer system may cause one or more services to be re-migrated again.

At block 914, the computer system may decommission the edge device (e.g., execute operations that cause the edge device to be decommissioned). In some embodiments, the operations of block 914 may be an optional step. In some embodiments, the decommissioning of the edge device may involve any suitable operations, including, for example, shutting down (e.g., powering off) the edge device, wiping and/or re-imaging the edge device, instructing the customer to ship the edge device back to the CSP (e.g., to make available for provisioning of the edge device to another customer), etc.

Figure 10:
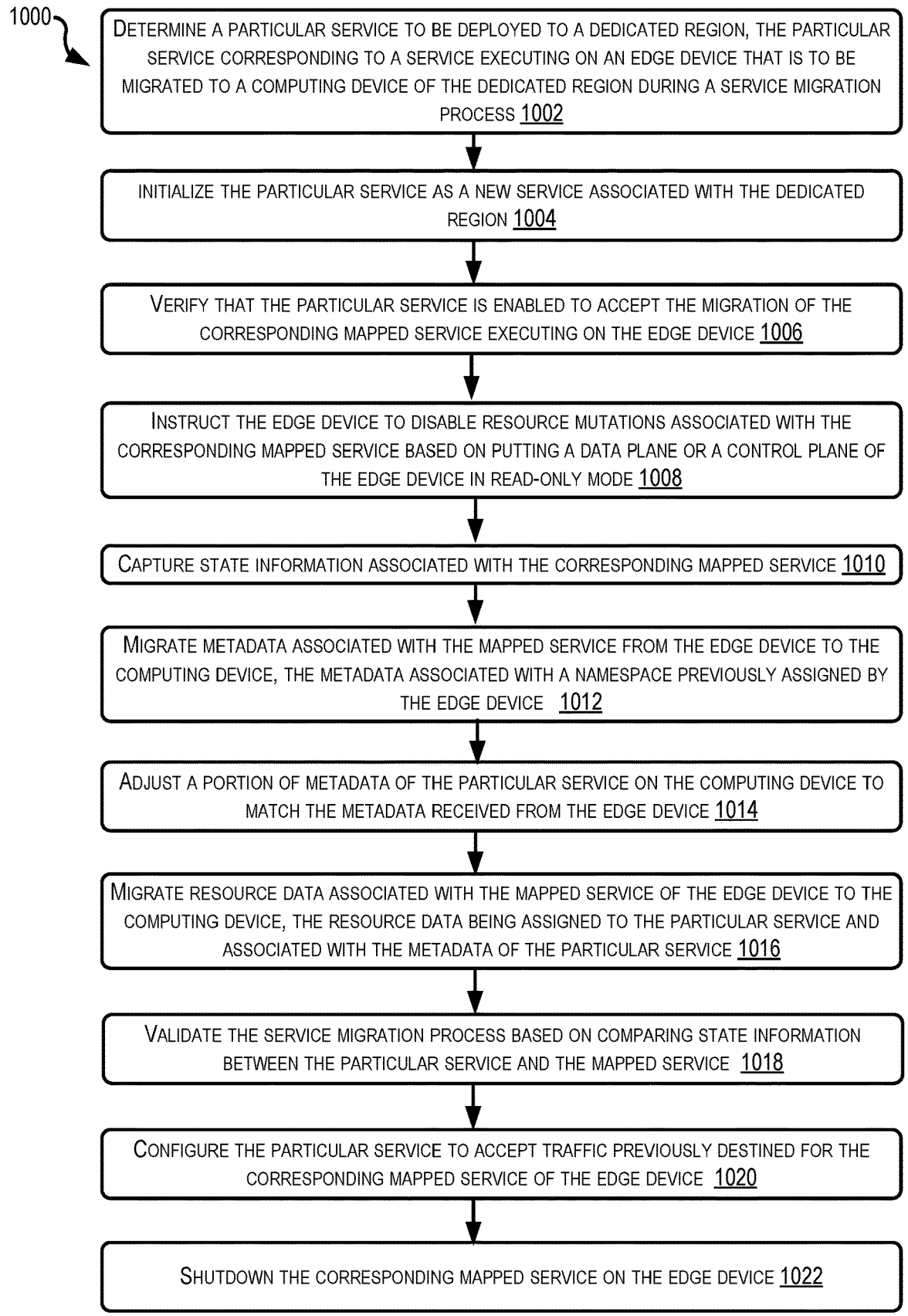
FIG. 10 is another flow diagram illustrating an example technique for facilitating a migration of a particular service from an edge device to a cloud computing environment, according to some embodiments.

FIG. 10 is another flow diagram illustrating an example process 1000 for facilitating a migration of a particular service from an edge device to a cloud computing environment, according to some embodiments. While process 900 of FIG. 9 focuses on an end-to-end migration process in the context of configuring a virtual bootstrap environment (e.g., including migrating a plurality of services (and/or corresponding resources) from an edge device, whereby service dependencies are accounted for), process 1000 provides more details regarding the migration process for migrating a particular service (and/or corresponding resources) from an edge device to a computing device associated with a dedicated region. In some embodiments, one or more of the operations of the blocks of process 1000 may be similar to one or more operations of block 910 of FIG. 9 and/or the migration process 817 of FIG. 1. In some embodiments, process 1000 may be performed by any suitable computing device associated with a cloud computing environment (e.g., migration service 811 of computer system 809 of FIG. 1). In some embodiments, process 1000 may involve executing instructions that cause one or more devices (e.g., edge device(s) 807, a computing device of the dedicated region 803, etc.) to further perform operations, for example, transmitting data between the devices. In some embodiments, FIG. 11 may further illustrate the operations of process 1000, described in further detail below.

Figure 11:
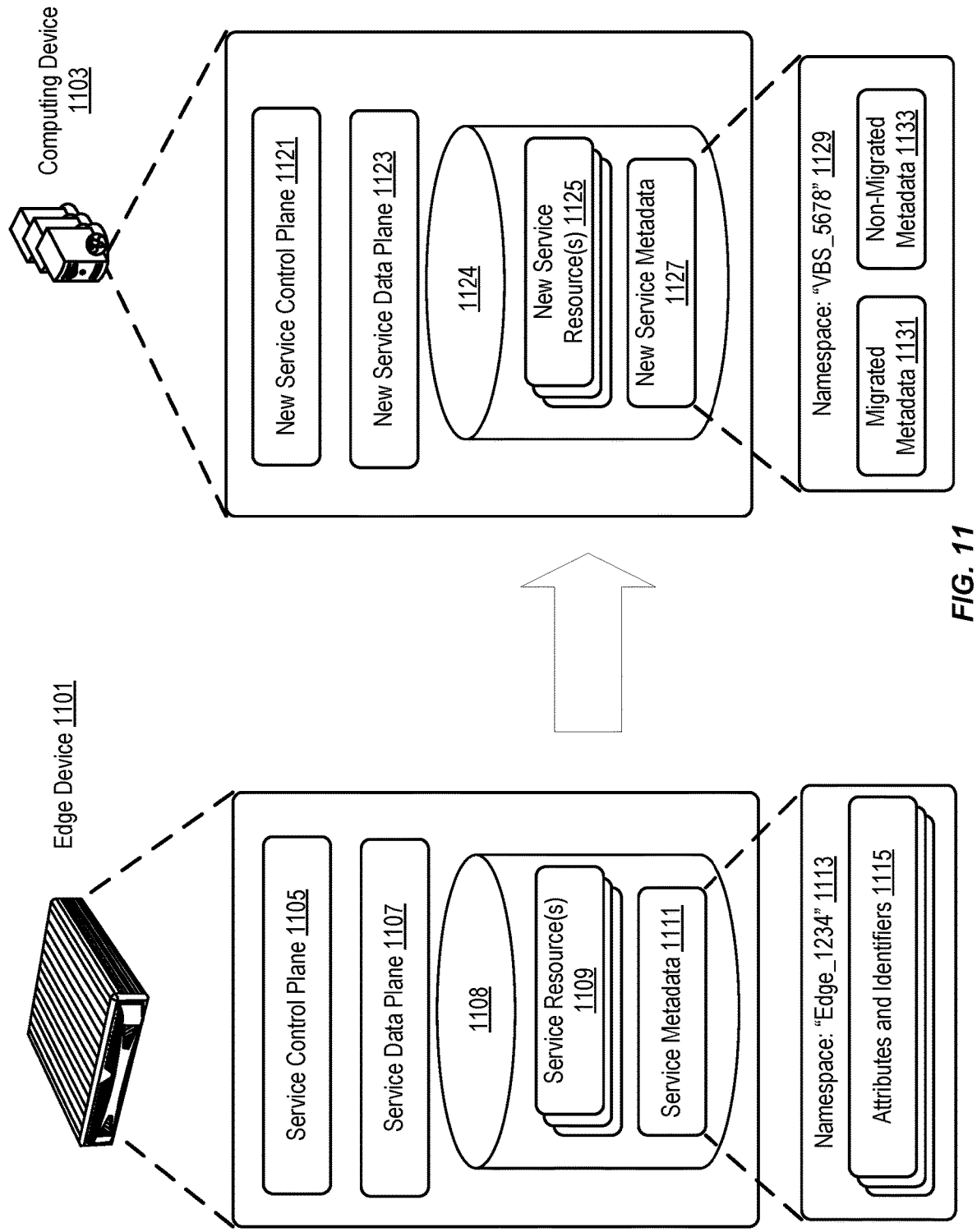
FIG. 11 is a block diagram illustrating a technique for migrating a service from an edge device to a computing device of a cloud computing environment, according to some embodiments.

FIG. 11 is a block diagram illustrating a technique for migrating a service (and/or corresponding resources) from an edge device to a computing device of a cloud computing environment, according to some embodiments. In FIG. 11, an edge device 1101 and computing device 1103 are depicted. In some embodiments, edge device 1101 may be similar to edge device 821 of FIG. 1, and computing device 1103 may be configured to implement the virtual bootstrap environment 805 of the dedicated region 803.

Turning to the elements of FIG. 11 in further detail, edge device 1101 may execute at least one service (e.g., service 823A of FIG. 1, a representative example service), whereby various elements of the representative example service are depicted with respect to edge device 1101. For example, the example service may execute a service control plane 1105 and/or a service data plane 1107, which may respectively perform similar operations to other control and/or data planes described herein. For example, the control plane 1105 may be used to configure functions performed by the data plane (e.g., via one or more policies, such as security/access policies, as described further below with respect to service metadata 1111). The data plane 1107 may be configured to perform functions that manage data storage, processing, etc., in accordance with the policies set by the control plane 1105. The service may further be associated with (e.g., manage and/or store) service resources 1109 and/or service metadata 1111 (e.g., stored in a data store of the edge device 1101, such as data store 1108). The service resources 1109 may include any suitable resource of the service (e.g., files, folders, VM objects, instances, workloads, state data, container objects, non-metadata data objects, etc.). In some embodiments, service resources 1109 may be associated with managing hardware and/or software resources. The service metadata 1110 may include any suitable data that describes and/or is associated with the data contents of the service resources 1109. In some embodiments, the service metadata 1111 may include attributes and identifiers 1115, which may be formatted using any suitable format(s) (e.g., attributes represented by alphanumeric strings, universally unique identifiers (UUIDs), etc.). In some embodiments, the service metadata 1111 may include configuration data associated with security policies for particular service resources 1109, resource data update policies, workload state information, general information about the service, and the like. In some embodiments, the service metadata 1111 may (or may not) be visible (e.g., presentable via a user interface) to a customer.

As depicted in FIG. 11, the service metadata 1111 (and/or service resources 1109) may be associated with a particular namespace (e.g., namespace 1113). In some embodiments, the namespace may be indicated by any suitable indicator (e.g., a unique alphanumeric string, a UUID, etc.), such as "Edge_1234," as indicated in FIG. 11. As described herein, a namespace may be used to ensure that identities of data objects are unique within the given namespace. In some embodiments, the attributes and identifiers 1115 may be associated with namespace 1113. For example, the alphanumeric string associated with namespace 1113 may be prepended to each of the attributes and identifiers 1115. It should be understood that any suitable technique (e.g., string concatenation, hashing, etc.) may be used to associate service metadata 1111 elements with the particular namespace 1113. As described herein, a given namespace may be applied across a plurality of services (e.g., executing on edge device 1101 and/or across a cluster of edge devices). Accordingly, metadata elements may be uniquely identified for the particular namespace, and distinct from other metadata elements of another namespace. In some embodiments, a given namespace may also be used to uniquely identity resource data objects (e.g., of service resources 1109), for example, via metadata elements that describe (and/or manage) the contents of the resource data objects. In some embodiments, elements associated with a given namespace may be organized in any suitable fashion. For example, elements may be nested in a hierarchical ordering to include sub-elements, etc.

Meanwhile, the computing device 1103 may execute (e.g., initialize and/or configure) one or more services associated with a dedicated region. In some embodiments, the dedicated region may be initially configured to be associated with a particular namespace (e.g., namespace 1129, "VBS_5678") that is different from namespace 1113 of edge device 1101. In some embodiments, one or more computing resources (e.g., including computing device 1103) may be used to implement the dedicated region that is used to configure a virtual bootstrap environment and receive migrated services from edge device 1101. As described further herein, with respect to process 1000 of FIG. 10, a particular predefined protocol may be used to migrate service(s) (and/or corresponding resources) from edge device 1101 to computing device 1103 during the service migration process for a particular service.

Returning now to process 1000 in further detail, at block 1002, a computer system determines a particular service (and/or corresponding resources) to be deployed to a computing device (e.g., computing device 1103 of FIG. 11) associated with a virtual bootstrap environment (e.g., an example of the virtual bootstrap environment 805 of FIG. 8), the particular service corresponding to a service executing on an edge device that is to be migrated to a computing device during a migration process. For example, computer system 809 may identify the particular service (e.g., a database management service, which may be service 819C) is the next service to be deployed, among a plurality of cloud computing services determined to be deployed to the virtual bootstrap environment 805. The next service may be determined according to a sort order as described in reference to FIG. 9 (e.g., block 906). In this example, the virtual bootstrap environment may be implemented at least in part by computing device 1103 of FIG. 11. The particular service being deployed may also be determined to have a matching (e.g., equivalent) counterpart service (e.g., another database management service) executed on the edge device (e.g., service 823A, corresponding to the example service depicted via edge device 1101 in FIG. 11). The counterpart service may be determined to be migrated as part of the deployment process of the particular service. In some embodiments, the computer system may receive telemetry data (e.g., health indicator data) from the edge device 1101 that indicates that the service to be migrated is executing normally and ready to be migrated.

At block 1004, the computer system may initialize the particular service as a new service within the virtual bootstrap environment. Continuing with the example above, whereby the particular service is a database management service, the computer system may deploy the database management service to the computing device 1103. For example, the initialization may include provisioning new service resources 1125, such as installing database files, etc. (e.g., installed to data store 1124). The initialization may further include generating new service metadata 1127 in association with the new service resources 1125 (e.g., setting database permissions, security policies, etc., as described herein). As described herein (e.g., similar to the counterpart database management service of edge device 1101), the new service may be configured to have a control plane 1121 and a data plane 1123. In some embodiments, one or more of the new service metadata 1127 may be associated with namespace 1129. As described further below, a portion of the metadata 1111 from edge device 1101 may subsequently be copied over to replace at least a portion of the new service metadata 1127.

At block 1006, the computer system may verify that the particular service is enabled to accept the migration of the corresponding mapped service executing on the edge device. For example, the computer system may receive a message from computing device 1103 (e.g., over a VPN) that indicates that the new service has been initialized and is ready to receive migration data from the edge device 1101. In some embodiments, the computer system may receive health indicator data (e.g., telemetry data) that indicates a status of the initialized service (e.g., a baseline health indicator), for example, indicating that all files have been properly installed, that the control plane 1121 and data plane 1123 are operating normally, etc. In some embodiments, the health data may indicate a warning (and/or error) if, for example, certain dependencies of the particular service have not yet been fully deployed.

At block 1008, the computer system may instruct the edge device to disable resource mutations associated with the corresponding mapped (e.g., counterpart) service based on putting a data plane or a control plane of the edge device in read-only mode. For example, the computer system 809 may transmit a message to edge device 1101, whereby the service control plane 1105 (and/or service data plane 1107) is instructed to enable a read-only mode. In the read-only mode, state data of the service (e.g., including service resource data 1109 and/or service metadata 1111) may be configured to be a read-only state. In some embodiments, the computer system may disable an active execution of the service (e.g., temporarily preventing customer input to change service policies) in order to enable read-only mode.

At block 1010, the computer system may capture state information (e.g., one type of resource) associated with the corresponding mapped service. For example, following the edge device service of edge device 1101 being put into a read-only mode, the computer system may capture (e.g., via an API call to a capturing service of the edge device) state information associate with the service resources 1109 and service metadata 1111 of the service. In some embodiments, the state information may include customer-visible state information from the perspective of the edge device 1101. In some embodiments, this information may be subsequently used to perform migration of data to the computing device 1103 and/or validate that the migration process for the service was performed successfully.

At block 1012, the computer system may migrate metadata (e.g., one type of resource) associated with the mapped service from the edge device to the computing device, the metadata associated with a namespace previously assigned by the edge device. Continuing with the illustration above, the computer system may instruct the edge device 1101 to transmit (e.g., via a previously established VPN, such as VPN 815 of FIG. 1) at least a portion (e.g., all) of the service metadata 1111, including attributes and identifiers 1115, to the computing device 1103. This may include customer-visible resources, attributes, and other identifiers of the service metadata 1111. In some embodiments, the metadata to be migrated may be predetermined according to a predefined protocol. For example, the predefined protocol may specify a list of identifiers and/or attributes that are to be migrated over. In some embodiments, the predefined protocol may involve executing a function to determine what metadata has been generated (and/or modified) by the customer since an initialization of the service on the edge device. Any suitable protocol may be used to determine what metadata should be migrated.

At block 1014, the computer system may adjust a portion of metadata of the particular service on the computing device to match the metadata received from the edge device. For example, recall that in this example, at block 1004, the computing device 1103 initialized the particular service (e.g., the databased management service), which included setting initial new service metadata 1127. At least a portion of the new service metadata 1127 may have a counterpart metadata (e.g., attributes, identifiers, policies, with matching names, etc.) of service metadata 1111. Accordingly, the migrated metadata may replace the portion of corresponding (e.g., matching) metadata of new service metadata 1127 (e.g., including substituting string values), thus depicted in FIG. 11 as migrated metadata 1131. Another portion of the new service metadata 1127 that does not overlap with the counterpart service metadata 1111 (e.g., and thus, is not replaced/substituted) is depicted in FIG. 11 as non-migrated metadata 1133. In some embodiments, the migrated metadata 1131 may (or may not) be associated with the new namespace 1129. In one example, the migrated metadata 1131 may be generated in part by "stitching" together old and new metadata. For example, a particular attribute value of service metadata 1111 may be substituted for a corresponding attribute value in service metadata 1127, whereby the namespace of the particular attribute value is changed from namespace 1113 to namespace 1129. In some embodiments, the namespace for a migrated attribute may not be adjusted (e.g., may remain associated with namespace 1113). In some embodiments, the computer system may ensure that the resulting service metadata 1127 (e.g., including both migrated metadata 1131 and non-migrated metadata 1133) is such that existing settings (e.g., including security and/or authorization policies, relationships between metadata) of the service from the edge device 1101 are preserved. In some embodiments, the migrated metadata 1131 may include additional (e.g., augmented) metadata to facilitate a successful migration process. For example, suppose that the database management service of computing device 1103 has additional settings that require configuration (e.g., due to a larger set of hardware features for the computing device 1103, compared with edge device 1101). In this example, the computer system may execute a process to translate (e.g., augment) the migrated attribute, given the change in hardware implementation. It should be understood that any suitable adjustments may be performed for new service metadata 1127 to ensure continuity of metadata from the migrated service. For example, sub-attributes may be adjusted within a hierarchy of attributes (e.g., name/value pairs) that are migrated. In some embodiments, upon completion of the metadata migration, the resulting metadata may be unique within the namespace 1129. The resulting metadata may further be configured such that the new service of computing device 1103 executes as the old service of edge device 1101 (e.g., thus enabling the service to accept traffic previously destined for the edge device service).

At block 1016, the computer system may migrate resource data (e.g., one type of resource) associated with the mapped service of the edge device to the computing device, the resource data being assigned to the particular service and associated with the metadata of the particular service. As described herein, the resource data may include any suitable data objects (e.g., files, containers, VM's, etc.). In some embodiments, the migration of resource data may be in accordance with a predefined protocol. In this example, the predefined protocol may include copying data between data planes (e.g., copying resource data 1109 from data plane 1107 to resource data 1125 of data plane 1123). In another example, the predefined protocol may include executing a process to construct (e.g., and/or re-construct, as the case may be) a data object. For example, the protocol may invoke an API available from the edge device 1101 and/or the dedicated region. The API may be used to obtain data resources in a particular format (e.g., a compressed format) from resource data 1109, transport the data to the computing device 1103, and then decompress the data for storage among the resource data 1125. In some embodiments, one or more operations of block 1016 may involve modifying service metadata (e.g., migrated metadata 1131 and/or non-migrated metadata 1133) to ensure that the metadata remains properly associated with the resulting resource data. It should be understood that any suitable protocol may be employed to migrate resource data between the edge device 1101 and the virtual bootstrap environment implemented by the computing device 1103.

At block 1018, the computer system may validate the migration process based on comparing state information between the particular service and the mapped service. For example, similarly as described herein with respect to block 912, the computer system may obtain first state data that corresponds to a current state of the migrated service (e.g., a first service) associated with the edge device. This may be similar to (e.g., the same as) the state information captured at block 1010. The computer system may further obtain second state data that corresponds to a current state of the migrated service (e.g., a second service) that is migrated to the computing device 1103 and associated with the virtual bootstrap environment. The computer system may then compare the first state data of the first service with the second state data of the second service to validate that they match (e.g., including matching metadata values, matching resource data inventory, etc.). In some embodiments, any suitable combination of the operations of 1002-1018 may be repeated to the migration process for migrating services/resources between the virtual bootstrap environment and a dedicated region (e.g., the dedicated region 803 of FIG. 8).

At block 1020, the computer system may configure the particular service (e.g., of the dedicated region 803) to accept traffic previously destined for the corresponding mapped service of the edge device. In some embodiments, the operations of block 1020 may (or may not) be performed in accordance with determining at block 1018 whether or not the validation was successful. In some embodiments, this may be similar to as described in reference to block 912.

At block 1022, the computer system may shutdown the corresponding mapped service on the edge device. In some embodiments, migrated service may be shut down upon confirmation that the migration was performed successfully. Note that, as described above, the process 1000 is described with respect to the migration of a particular (e.g., single) service. Accordingly, as each service may be migrated (e.g., according to the sort order described in process 900), the services may be shut down at the edge device. In some embodiments, upon all migrated services being successfully migrated and shut down, the edge device may be decommissioned, as described in reference to block 914 of FIG. 9.

As described above, process 1000 of FIG. 10 and the illustration of FIG. 11 are described with respect to facilitating a service migration from a particular edge device to a computing device configured to execute a virtual bootstrap environment of a dedicated region. However, service migration scenarios according to embodiments herein should not be construed to be so limited. For example, as described herein, the particular edge device may belong to a particular distributed computing cluster. The distributed computing cluster of edge devices may be collectively associated with a particular namespace, whereby services are migrated from the cluster of devices to a new dedicated region (e.g., including one or more computing devices). This may be performed at least in part because a given namespace may guarantee no identity and/or policy conflicts. Thus, migration to another new dedicated region may preserve such guarantees. In another example, multiple clusters that belong to the same namespace may have services migrated to a particular dedicated region. In a case where multiple clusters, respectively, are associated with different namespaces, a merger of different clusters into the same namespace (e.g., of a particular dedicated region) may involve one or more operations to resolve conflicts, rename identities and/or provision different identities to ensure that unique identities are preserved within the destination namespace of the dedicated region. In some embodiments, even if devices of a cluster are associated with the same name namespace, there may be conflicting policies caused by the different clusters having being altered by the customer in conflicting ways. These conflicting policies may necessitate resolution to migrate the clusters to the same destination dedicated region.

To further illustrate an example in which a plurality of clusters (e.g., of the same namespace) are migrated to the same namespace of a particular dedicated region, consider a case in which conflict resolution protocol may be employed among different conflicting policies. For example, suppose that there is a policy added in a first cluster that provides that "ALL devices in GROUP Servers are ALLOWED to AUTO-UPDATE." Suppose that another policy was added to a second cluster that provides that "ALL devices in GROUP Servers are DISALLOWED to AUTO-UPDATE." Since all the devices have unique names across the first cluster and the second cluster, the services may be migrated to a target dedicated region. However, in some embodiments, both of these policies may not be valid at the same time because the GROUP name ("Server") is not unique across both clusters. Thus, a conflict resolution protocol may be employed, whereby one of a plurality of options may be chosen. For example, the options may include blocking the migration indefinitely, raising a conflict and allowing the customer (and/or customer agent) to disambiguate by changing the policy of either cluster to avoid the conflict, or instructing the customer to disambiguate so that migration is possible. For example, the customer could change the GROUP name in the first cluster to "Cluster1-Servers" and the GROUP name in the second cluster to "Cluster2-Servers," since both of the resulting policies could coexist without changing behavior. In some embodiments, the conflict resolution protocol may automatically determine how to resolve conflicts (e.g., automatically overriding one policy in favor of another, based on a pre-determined protocol).

In another example involving a conflict resolution protocol, suppose that the target dedicated region is not a new dedicated region, but in fact is an existing dedicated region. In this example, the above conflict resolution protocol may involve resolving policy conflicts between a source cluster and the existing dedicated region. It should be understood that the examples described above are representative examples of different types of conflict resolution protocols that may be employed to resolve conflicts within the same namespace and/or across namespaces when performing a service migration process to a destination region.

Figure 12:
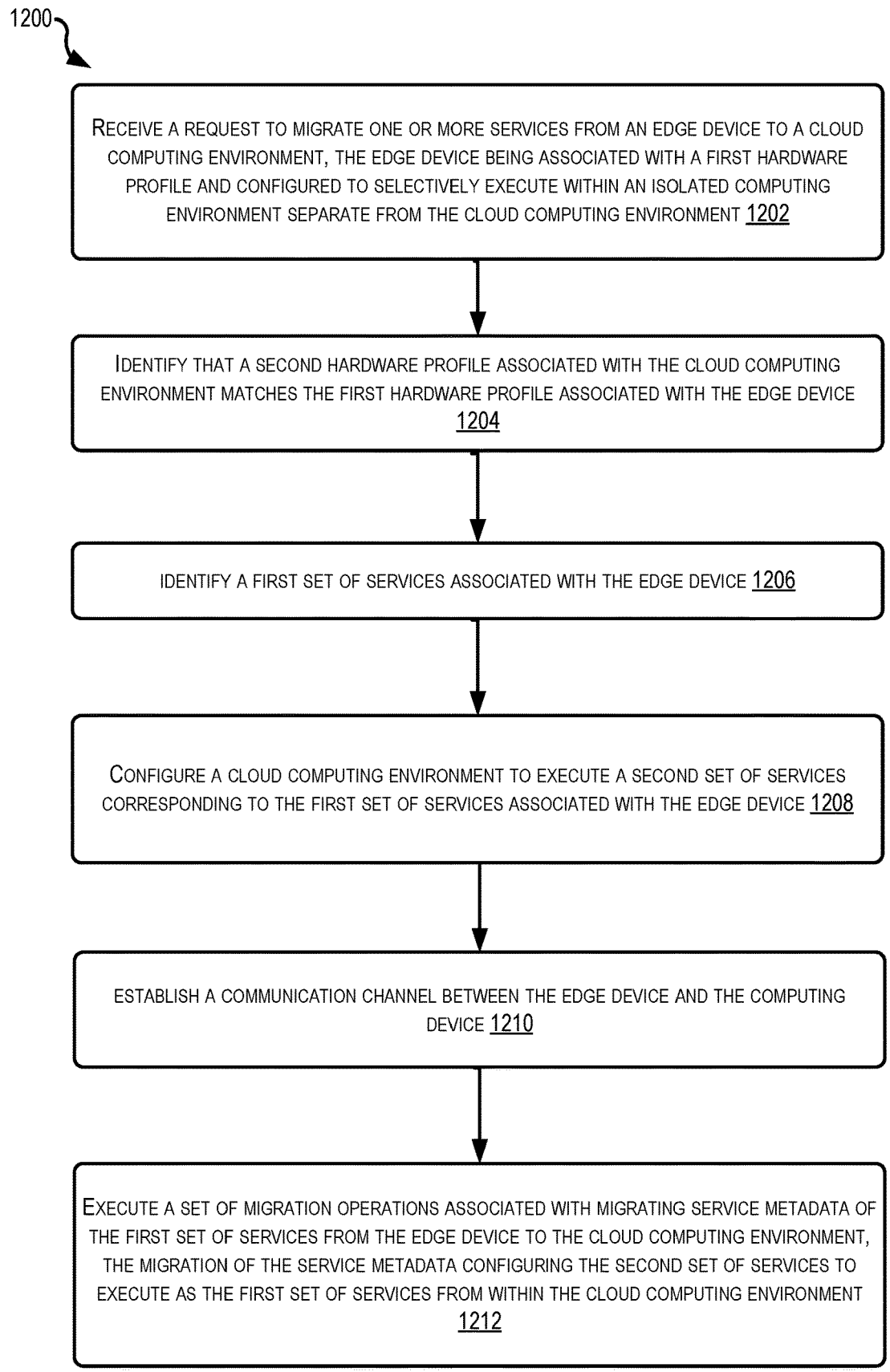
FIG. 12 is another flow diagram illustrating an example technique for facilitating a migration of one or more services from an edge device to a cloud computing environment, according to some embodiments.

FIG. 12 is another flow diagram illustrating an example technique for facilitating a migration of one or more resources from an edge device to a cloud computing environment, according to some embodiments. In some embodiments, process 1200 may be performed by any suitable computing device associated with a cloud computing environment (e.g., migration service 811 of computer system 809 of FIG. 1). In some embodiments, process 1200 may involve executing instructions that cause one or more devices (e.g., edge device 821, a computing device of the dedicated region 803, etc.) to further perform operations, for example, transmitting data between the devices.

At block 1202, a computer system may receive, by a migration service of a cloud computing environment, a request to migrate one or more services (and/or resources associated with one or more services) from an edge device to the cloud computing environment (e.g., the virtual bootstrap environment 805 of FIG. 8, the dedicated region 803 of FIG. 8, etc.). In some embodiments, the edge device may be associated with a first hardware profile and configured to selectively execute within an isolated computing environment separate from the cloud computing environment. In some embodiments, one or more operations of block 1202 may be similar to as described in reference to step S1 of FIG. 8. For example, user device 801 of a particular customer may transmit the request to computer system 809, whereby the edge device (e.g., edge device 821) is currently provisioned to the particular customer. In one example, the customer may intend to decommission and/or return the edge device to the cloud services provider upon confirming that the migration of the one or more services to the cloud computing environment was successful.

At block 1204, the computer system may identify, by the migration service, that a second hardware profile associated with the cloud computing environment (e.g., a hardware profile of one or more computing devices of the cloud computing environment) matches the first hardware profile associated with the edge device. In some embodiments, one or more operations of block 1204 may be similar to as described in reference to step S2 of FIG. 8. For example, the computer system may identify that a computing device (e.g., a computing device associated with the virtual bootstrap environment, a computing device of the dedicated region) has a matching hardware profile with the edge device. The two hardware profiles may be considered matching if they differ from one another by less than a threshold amount corresponding to any suitable unit of measurement. For example, the various features (e.g., number of CPU cores (e.g., 40 CPU cores), a number of memory units (e.g., 512 Gigabytes), data bus types, disk storage types, network card types, other processor types (e.g., GPU resource), etc.) of a hardware profile may be weighted together and/or individually assessed with a numeric score (e.g., included within a vector of scores). The vector representation for a given profile may be compared against another vector to determine a similarity between the vectors (e.g., a cosine similarity). It should be understood that any suitable method may be used to determine whether one device has a matching hardware profile with another computing device. In some embodiments, the cloud computing environment (e.g., the virtual bootstrap environment, the dedicated region) may be provisioned at the time of receiving the request to migrate services (e.g., as a new virtual bootstrap environment or dedicated region, with a new namespace). In some embodiments, the cloud computing environment may be already existing prior to receiving the request.

At block 1206, the computer system may identify a first set of services associated with the edge device. For example, as described in reference to process 900 (e.g., block 902), the computer system may receive a manifest file that indicates the first set of services executing at the edge device. The manifest file may be received at any suitable time. For example, the edge device may transmit the manifest file upon being requested by the computer system to perform an inventory check to determine what services are currently executing and/or require migration.

At block 1208, the computer system may configure the cloud computing environment (e.g., the virtual bootstrap environment 805) to execute a second set of services corresponding to the first set of services associated with the edge device. In some embodiments, one or more operations of block 1208 may be similar to as described in reference to step S2 of FIG. 8. For example, the computer system may cause the computing device (e.g., identified at block 1204 as having a matching profile with the edge device) to be provisioned with an OS and a core set of services. This initial configuration may be enable communication to be established between the edge device and the computing device. In some embodiments, the core set of services may enable other (e.g., additional) services to be installed (e.g., provisioned) to the computing device. In some embodiments, the full set of services scheduled to be provisioned (e.g., imaged and/or installed) to the computing device may be a set of services provided by the cloud services provider. In some embodiments, a subset of the full set of services (e.g., the second set of services) may correspond to (e.g., be substantially equivalent to) the first set of services associated with (e.g., executing on) the edge device. In some embodiments, the computing device may be configured with the full set of services (e.g., including the second set of services) according to a suitable installation order (e.g., a topological sort order), for example, as described with respect to process 900 of FIG. 9.

At block 1210, the computer system may establish a communication channel (e.g., a VPN channel) between the edge device and the computing device. In some embodiments, one or more operations of block 1210 may be similar to as described in reference to step S3 of FIG. 8.

At block 1212, the computer system may execute, by the migration service, a set of migration operations associated with migrating service metadata of the first set of services from the edge device to the cloud computing environment (e.g., the virtual bootstrap environment). In some embodiments, migrating the service metadata configures the second set of services to execute as the first set of services from within the dedicated region of the cloud computing environment. In some embodiments, the migration operations associated with migrating the first set of services may be similar to as described with respect to FIG. 9. In some embodiments, the migration operations for a migrating a particular service (and/or corresponding resources) of the first set of services may be similar to as described with respect to FIGS. 10 and 11. For example, in some embodiments, the set of migration operations may include instructing the edge device to disable resource mutations associated with the first set of services executing at the edge device, wherein disabling resource mutations includes transitioning each of the first set of services to execute in a read-only mode. The operations may further include adjusting at least a portion of default configuration data of the cloud computing environment (e.g., a portion of service metadata of an initialized service, as described in reference to block 1004 of FIG. 10) to match the service metadata migrated from the edge device. Upon confirming successful migration of service metadata and resource data, the operations may configure the second set of services of the cloud computing environment (e.g., implemented by the virtual bootstrap environment, implemented by the dedicated region) to accept traffic previously intended for the first set of services of the edge device. In some embodiments, the computer system may validate that a service was successfully migrated, for example, by comparing state data obtained from both the edge device and the computing device (e.g., see block 1018 of FIG. 10). In some embodiments, the operations of method 1200 may be performed between the edge device and a virtual bootstrap environment. In some embodiments, the operations of method 1200 may be performed between the virtual bootstrap environment and the dedicated region (e.g., subsequent to performing the method 1200, or any suitable portion of the method 1200, between the edge device and the virtual bootstrap environment). In some embodiments, the operations of method 1200 may be performed between the edge device and the dedicated region without utilizing the virtual bootstrap environment.

As described herein, in some embodiments, the edge device may be associated with a distributed computing cluster of edge devices (e.g., as a first edge device of the cluster), whereby services from each device are migrated to the dedicated region. For example, another computing device of the dedicated region may be configured with a third set of services corresponding to a second edge device of a plurality of edge devices of the distributed computing cluster. The computer system may establish a second communication channel (e.g., another VPN channel) between the second edge device of the distributed computing cluster and a second virtual bootstrap environment (e.g., of the other computing device) associated with the dedicated region. Similar to as described herein, the computer system may execute a second set of migration operations associated with migrating corresponding service metadata of a fourth set of services from the second edge device to the second virtual bootstrap environment. In this example, migrating the corresponding service metadata of the fourth set of services to the second virtual bootstrap environment may configure the third set of services of the dedicated region to execute as the fourth set of services from within the cloud computing environment. In some embodiments, as described herein, multiple edge devices of a cluster may be migrated to the dedicated region, whereby identity and/or policy conflicts may be resolved according to a predefined protocol.

Although specific embodiments have been described, various modifications, alterations, alternative constructions, and equivalents are also encompassed within the scope of the disclosure. Embodiments are not restricted to operation within certain specific data processing environments, but are free to operate within a plurality of data processing environments. Additionally, although embodiments have been described using a particular series of transactions and steps, it should be apparent to those skilled in the art that the scope of the present disclosure is not limited to the described series of transactions and steps. Various features and aspects of the above-described embodiments may be used individually or jointly.

Further, while embodiments have been described using a particular combination of hardware and software, it should be recognized that other combinations of hardware and software are also within the scope of the present disclosure. Embodiments may be implemented only in hardware, or only in software, or using combinations thereof. The various processes described herein can be implemented on the same processor or different processors in any combination. Accordingly, where components or modules are described as being configured to perform certain operations, such configuration can be accomplished, e.g., by designing electronic circuits to perform the operation, by programming programmable electronic circuits (such as microprocessors) to perform the operation, or any combination thereof. Processes can communicate using a variety of techniques including but not limited to conventional techniques for inter process communication, and different pairs of processes may use different techniques, or the same pair of processes may use different techniques at different times.

The specification and drawings are, accordingly, to be regarded in an illustrative rather than a restrictive sense. It will, however, be evident that additions, subtractions, deletions, and other modifications and changes may be made thereunto without departing from the broader spirit and scope as set forth in the claims. Thus, although specific disclosure embodiments have been described, these are not intended to be limiting. Various modifications and equivalents are within the scope of the following claims.

The use of the terms "a" and "an" and "the" and similar referents in the context of describing the disclosed embodiments (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments and does not pose a limitation on the scope of the disclosure unless otherwise claimed. No language in the specification should be construed as indicating any non-claimed element as essential to the practice of the disclosure.

Disjunctive language such as the phrase "at least one of X, Y, or Z," unless specifically stated otherwise, is intended to be understood within the context as used in general to present that an item, term, etc., may be either X, Y, or Z, or any combination thereof (e.g., X, Y, and/or Z). Thus, such disjunctive language is not generally intended to, and should not, imply that certain embodiments require at least one of X, at least one of Y, or at least one of Z to each be present.

Preferred embodiments of this disclosure are described herein, including the best mode known for carrying out the disclosure. Variations of those preferred embodiments may become apparent to those of ordinary skill in the art upon reading the foregoing description. Those of ordinary skill should be able to employ such variations as appropriate and the disclosure may be practiced otherwise than as specifically described herein. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein.

All references, including publications, patent applications, and patents, cited herein are hereby incorporated by reference to the same extent as if each reference were individually and specifically indicated to be incorporated by reference and were set forth in its entirety herein.

In the foregoing specification, aspects of the disclosure are described with reference to specific embodiments thereof, but those skilled in the art will recognize that the disclosure is not limited thereto. Various features and aspects of the above-described disclosure may be used individually or jointly. Further, embodiments can be utilized in any number of environments and applications beyond those described herein without departing from the broader spirit and scope of the specification. The specification and drawings are, accordingly, to be regarded as illustrative rather than restrictive.

What is claimed is:

1. A computer-implemented method, comprising:
receiving, by a migration service of a cloud computing environment, a request to migrate one or more services from an edge device to the cloud computing environment, the edge device being associated with a first hardware profile and configured to selectively execute within an isolated computing environment separate from the cloud computing environment;
identifying, by the migration service, that a second hardware profile associated with the cloud computing environment matches the first hardware profile associated with the edge device;
identifying a first set of services associated with the edge device;
configuring, at a computing device, the cloud computing environment to execute a second set of services corresponding to the first set of services associated with the edge device;
establishing a communication channel between the edge device and the computing device;
executing, by the migration service, a set of migration operations associated with migrating service metadata of the first set of services from the edge device to the cloud computing environment, wherein migrating the service metadata configures the second set of services to execute as the first set of services from within the cloud computing environment;
instructing, by the migration service, the edge device to disable resource mutations associated with the first set of services executing at the edge device, wherein disabling the resource mutations comprises transitioning each of the first set of services to execute in a read-only mode;
adjusting, by the migration service, at least a portion of default configuration data of the cloud computing environment to match the service metadata migrated from the edge device; and
configuring, by the migration service, the second set of services of the cloud computing environment to accept traffic previously intended for the first set of services of the edge device.

2. The computer-implemented method of claim 1, wherein executing the set of migration operations further comprises:
obtaining, by the migration service, first state data that corresponds to a current state of the first set of services associated with the edge device;
obtaining, by the migration service, second state data that corresponds to a current state of the second set of services associated with the cloud computing environment;
comparing, by the migration service, the first state data with the second state data to validate that the current state of the second set of services matches the current state of the first set of services; and
in accordance with determination of a successful validation, configuring the second set of services of the cloud computing environment to accept traffic previously intended for the first set of services of the edge device.

3. The computer-implemented method of claim 1, wherein the edge device is a first edge device of a plurality of edge devices collectively configured to operate as a distributed computing cluster, the distributed computing cluster associated with a particular namespace, and wherein the method further comprises:
configuring the cloud computing environment with a third set of services corresponding to a second edge device of the plurality of edge devices of the distributed computing cluster;
establishing a second communication channel between the second edge device of the distributed computing cluster and a second cloud computing environment; and
executing, by the migration service, a second set of migration operations associated with migrating corresponding service metadata of a fourth set of services from the second edge device to the second cloud computing environment, wherein migrating the corresponding service metadata of the fourth set of services to the second cloud computing environment configures the third set of services of the cloud computing environment to execute as the fourth set of services from within the cloud computing environment.

4. The computer-implemented method of claim 1, further comprising:
initializing, based at least in part on predefined protocol, an additional service within the cloud computing environment;
determining that the additional service has no corresponding service executing on the edge device; and
configuring the additional service with data that is different from the service metadata migrated from the edge device.

5. The computer-implemented method of claim 1, further comprising:
accessing a manifest file associated with the edge device, the manifest file identifying the first hardware profile of the edge device and the first set of services executing at the edge device.

6. The computer-implemented method of claim 1, wherein executing the set of migration operations further comprises:
executing, by the migration service, one or more service-specific migration protocols, a particular migration protocol being associated with migrating resource data of a particular service of the first set of services from the edge device to the cloud computing environment.

7. A computer system of a cloud computing environment, comprising:
a memory comprising computer-executable instructions; and
one or more processors in communication with the memory and configured to access the memory and execute the computer-executable instructions to:

receive a request to migrate one or more services from an edge device to the cloud computing environment, the edge device being associated with a first hardware profile and configured to selectively execute within an isolated computing environment separate from the cloud computing environment;

identify that a second hardware profile of the cloud computing environment matches the first hardware profile associated with the edge device;

identify a first set of services associated with the edge device;

configure, at a computing device, the cloud computing environment to execute a second set of services corresponding to the first set of services associated with the edge device;

establish a communication channel between the edge device and the computing device;

execute a set of migration operations associated with migrating service metadata of the first set of services from the edge device to the cloud computing environment, wherein migrating the service metadata configures the second set of services to execute as the first set of services from within the cloud computing environment;

instruct the edge device to disable resource mutations associated with the first set of services executing at the edge device, wherein disabling the resource mutations comprises transitioning each of the first set of services to execute in a read-only mode;

adjust at least a portion of default configuration data of the cloud computing environment to match the service metadata migrated from the edge device; and configure the second set of services of the cloud computing environment to accept traffic previously intended for the first set of services of the edge device.

8. The computer system of claim 7, wherein executing the set of migration operations further comprises:

obtaining first state data that corresponds to a current state of the first set of services associated with the edge device;

obtaining second state data that corresponds to a current state of the second set of services associated with the cloud computing environment;

comparing the first state data with the second state data to validate that the current state of the second set of services matches the current state of the first set of services; and in accordance with determination of an unsuccessful validation, performing one or more remedial actions associated with correcting a mismatch between the second state data of the second set of services and the first state data of the first set of services.

9. The computer system of claim 7, wherein the edge device is a first edge device of a plurality of edge devices collectively configured to operate as a distributed computing cluster, the distributed computing cluster associated with a particular namespace, and wherein the instructions further comprise:

configuring the cloud computing environment with a third set of services corresponding to a second edge device of the plurality of edge devices of the distributed computing cluster;

establishing a second communication channel between the second edge device of the distributed computing cluster and a second cloud computing environment; and executing a second set of migration operations associated with migrating corresponding service metadata of a fourth set of services from the second edge device to the second cloud computing environment, wherein migrating the corresponding service metadata of the fourth set of services to the second cloud computing environment configures the third set of services of the cloud computing environment to execute as the fourth set of services from within the cloud computing environment.

10. The computer system of claim 7, wherein the instructions further comprise:

initializing, based at least in part on predefined protocol, an additional service within the cloud computing environment;

determining that the additional service has no corresponding service executing on the edge device; and configuring the additional service with data that is different from the service metadata migrated from the edge device.

11. The computer system of claim 7, wherein the instructions further comprise:

accessing a manifest file associated with the edge device, the manifest file identifying the first hardware profile of the edge device and the first set of services executing at the edge device.

12. The computer system of claim 7, wherein executing the set of migration operations further comprises:

executing one or more service-specific migration protocols, a particular migration protocol being associated with migrating resource data of a particular service of the first set of services from the edge device to the cloud computing environment.

13. One or more non-transitory computer-readable storage media comprising computer-executable instructions that, when executed by one or more processors of a cloud computing environment, causes the one or more processors to:

receive a request to migrate one or more services from an edge device to the cloud computing environment, the edge device being associated with a first hardware profile and configured to selectively execute within an isolated computing environment separate from the cloud computing environment;

identify that a second hardware profile of the cloud computing environment matches the first hardware profile associated with the edge device;

identify a first set of services associated with the edge device;

configure, at a computing device, the cloud computing environment to execute a second set of services corresponding to the first set of services associated with the edge device;

establish a communication channel between the edge device and the computing device;

execute a set of migration operations associated with migrating service metadata of the first set of services from the edge device to the cloud computing environment, wherein migrating the service metadata configures the second set of services to execute as the first set of services from within the cloud computing environment;

instruct the edge device to disable resource mutations associated with the first set of services executing at the edge device, wherein disabling the resource mutations comprises transitioning each of the first set of services to execute in a read-only mode;

adjust at least a portion of default configuration data of the cloud computing environment to match the service metadata migrated from the edge device; and configure the second set of services of the cloud computing environment to accept traffic previously intended for the first set of services of the edge device.

14. The one or more non-transitory computer-readable storage media of claim 13, wherein the edge device is a first edge device of a plurality of edge devices collectively configured to operate as a distributed computing cluster, the distributed computing cluster associated with a particular namespace, and wherein executing the computer-executable instructions further causes the one or more processors to:

configure the cloud computing environment with a third set of services corresponding to a second edge device of the plurality of edge devices of the distributed computing cluster;

establish a second communication channel between the second edge device of the distributed computing cluster and a second cloud computing environment; and execute a second set of migration operations associated with migrating corresponding service metadata of a fourth set of services from the second edge device to the second cloud computing environment, wherein migrating the corresponding service metadata of the fourth set of services to the second cloud computing environment configures the third set of services of the cloud computing environment to execute as the fourth set of services from within the cloud computing environment.

15. The one or more non-transitory computer-readable storage media of claim 13, wherein executing the computer-executable instructions further causes the one or more processors to:

initialize, based at least in part on predefined protocol, an additional service within the cloud computing environment;

determine that the additional service has no corresponding service executing on the edge device; and configure the additional service with data that is different from the service metadata migrated from the edge device.

16. The one or more non-transitory computer-readable storage media of claim 13, wherein executing the computer-executable instructions further causes the one or more processors to:

access a manifest file associated with the edge device, the manifest file identifying the first hardware profile of the edge device and the first set of services executing at the edge device.

17. The one or more non-transitory computer-readable storage media of claim 13, wherein executing the set of migration operations further comprises:

executing one or more service-specific migration protocols, a particular migration protocol being associated with migrating resource data of a particular service of the first set of services from the edge device to the cloud computing environment.

* * * * *

UNITED STATES PATENT AND TRADEMARK OFFICE
CERTIFICATE OF CORRECTION

PATENT NO. : 12,143,264 B2
APPLICATION NO. : 17/581804
DATED : November 12, 2024
INVENTOR(S) : Adogla et al.

Page 1 of 1

It is certified that error appears in the above-identified patent and that said Letters Patent is hereby corrected as shown below:

In the Claims

In Column 39, Line 52, in Claim 1, delete "cach" and insert -- each --, therefor.

Signed and Sealed this
Fourth Day of February, 2025

Coke Morgan Stewart
*Acting Director of the United States Patent and Trademark Office*